United States Patent
Kharul

(10) Patent No.: US 8,450,494 B2
(45) Date of Patent: May 28, 2013

(54) DISUBSTITUTED BENZAMIDE DERIVATIVES AS GLUCOKINASE (GK) ACTIVATORS

(75) Inventor: Rajendra Kharul, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 13/378,984

(22) PCT Filed: Jun. 21, 2010

(86) PCT No.: PCT/IN2010/000426
§ 371 (c)(1),
(2), (4) Date: Mar. 2, 2012

(87) PCT Pub. No.: WO2010/150280
PCT Pub. Date: Dec. 29, 2010

(65) Prior Publication Data
US 2012/0149704 A1    Jun. 14, 2012

(51) Int. Cl.
*C07D 271/10* (2006.01)
*C07D 271/113* (2006.01)
*C07D 401/14* (2006.01)
*A61K 31/445* (2006.01)
*A61K 31/41* (2006.01)

(52) U.S. Cl.
USPC ........... 548/143; 548/145; 546/210; 514/326; 514/364

(58) Field of Classification Search
None
See application file for complete search history.

(56) References Cited

U.S. PATENT DOCUMENTS

| | | |
|---|---|---|
| 2007/0287693 A1 | 12/2007 | Johnstone |
| 2008/0015203 A1 | 1/2008 | Johnstone |
| 2008/0171734 A1 | 7/2008 | Campbell |
| 2008/0234273 A1 | 9/2008 | McKerrecher |
| 2008/0280872 A1 | 11/2008 | Johnstone |
| 2008/0280874 A1 | 11/2008 | Johnstone |
| 2008/0312207 A1 | 12/2008 | Johnstone |
| 2009/0253676 A1 | 10/2009 | Johnstone |

FOREIGN PATENT DOCUMENTS

| | | |
|---|---|---|
| EP | 1305301 B1 | 6/2005 |
| WO | 2001044216 A1 | 6/2001 |
| WO | 2005080359 A1 | 9/2005 |
| WO | 2005080360 A1 | 9/2005 |
| WO | 2005121110 A1 | 12/2005 |
| WO | 2006040528 A1 | 4/2006 |
| WO | 2006040529 A1 | 4/2006 |
| WO | 2007007042 A1 | 1/2007 |
| WO | 2007125105 A2 | 11/2007 |
| WO | 2008050101 A1 | 5/2008 |

OTHER PUBLICATIONS

European Patent Office, PCT/IN2010/000426, International Search Report, Nov. 24, 2010.
European Patent Office, PCT/IN2010/000426, International Preliminary Report on Patentability, Sep. 30, 2011.
Iino T et al, "Discovery of potent and orally active 3-alkoxy-5-phenoxy-N-thiazolyl benzamides as novel allosteric glucokinase activators", Bioorganic & Medicinal Chemistry, PERGAMON, GB LNKD-DOI, vol. 17,k No. 7, pp. 2733-2743, Feb. 25, 2009.
Iino T et al, "Metabolic activation of N-thiazol-2-yl benzamide as glucokinase activators: Impacts of glutathione trapping on covalent binding" Bioorganic & Medicinal Chemistry Letters, Pergamon, Elsevier Science, GB LNKD-KOI, vol. 20, No. 5, pp. 1619-1622, Jan. 20, 2010.

*Primary Examiner* — Nyeemah A Grazier
(74) *Attorney, Agent, or Firm* — IpHorgan Ltd.

(57) ABSTRACT

The invention relates to disubstituted benzamide derivatives of the general Formula (I), their pharmaceutically acceptable salts, pharmaceutically acceptable solvates, enantiomers, diastereomers, prodrugs, metabolites and polymorphs. The invention also relates to processes for the preparation of the compounds of the invention, pharmaceutical compositions containing the compounds and to methods for treating type II diabetes using the compounds of the invention.

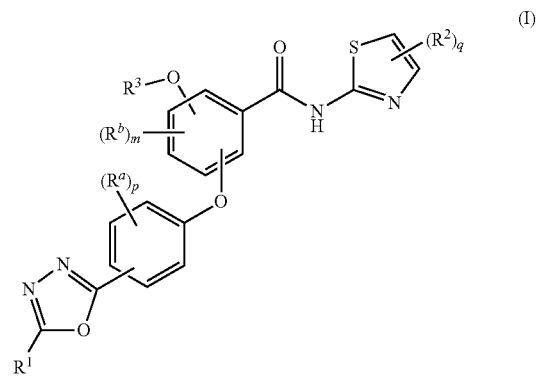

10 Claims, No Drawings

DISUBSTITUTED BENZAMIDE DERIVATIVES AS GLUCOKINASE (GK) ACTIVATORS

FIELD OF THE INVENTION

The present invention relates to disubstituted benzamide derivatives of the general Formula (I), their pharmaceutically acceptable salts, pharmaceutically acceptable solvates, enantiomers, diastereomers, prodrugs, metabolites and polymorphs. The invention also relates to processes for the preparation of the compounds of the invention, pharmaceutical compositions containing the compounds and to methods for treating type II diabetes using the compounds of the invention.

BACKGROUND OF THE INVENTION

Glucokinase (GK) also referred as hexokinase IV or hexokinase D belongs to the family of hexokinases. It catalyzes phosphorylation of hexoses such as D-glucose, D-mannose, D-fructose and 2-deoxy-D-glucose by $MgATP^{2-}$. (Cardenas, M. L. et. al., *Biochim. Biophys. Acta,* 1401, 242-264 (1998)). Glucokinase differs from other hexokinases in terms of its enzyme kinetics. It has positive co-operativity and low affinity for glucose. In contrast to other hexokinases, it does not get inhibited by its end product, glucose-6-phosphate.

Glucokinase is principally expressed in liver and pancreatic β-cells. The glucose concentration at which glucokinase exhibits half maximum activity is 8 mM. The other three hexokinases get saturated at very low glucose concentration (<1 mM). Therefore, the flux of glucose through GK pathway rises as the concentration of glucose in the blood increases from fasting (5 mM) to postprandial (~10 mM) levels following carbohydrate containing meal [Printz, R. G., Magnuson, M. A. and Granner, D. K. in *Ann. Rev. Nutrition*, vol. 13, (R. E. Olson, D. M. Bier, and D. B. McCormik, eds.) Annual Review Inc. Palo Alto, Calif., pages 463-496, 1993]. A decade ago, these and subsequent findings led to the hypothesis that GK functions as glucose sensor in hepatocyte and pancreatic β-cells. (Meglasson, M. D. et. al. *Amer. J. Physiol.,* 246, E1-E13, 1984).

Recently, transgenic animal study has confirmed that GK does play a critical role in whole-body glucose-homeostasis. Animals those do not express GK die within few days of birth with severe diabetes while animals with GK overexpression have improved glucose tolerance [Grupe, A. et. al. *Cell,* 83, 69-78, (1995); Ferrie, T. et. al. *FASEB J.,* 10, 1213-1218, (1996)].

There are both, activating and deactivating mutations reported for GK gene. Deactivating mutations cause diabetes called type 2 maturity onset diabetes of young (MODY2) (Vionnet, N., et. al., *Nature,* 356, 721-22, (1992); Matschinsky, F. M., et. al. *J. Clin. Invest.* 92, 2092-98, (1993)) while activating mutations cause persistent hyperinsulinemia hypoglycemia of infancy (PHHI) (Christesen, H. B. et. al., *Diabetes,* 51, 1240-46, (2002)). These literature data supports the notion that small molecules as glucokinase activators will help to treat diabetes particularly type II diabetes.

International (PCT) Patent Publication No. WO 01/44216 discloses 2,3-disubstituted trans olefin N-heteroaromatic or urido proprionamides as glucokinase activators which increase insulin secretion in the treatment of type II diabetes. U.S. Pat. No. 0,225,286 discloses hydantoin compounds which are active as glucokinase activators and useful to increase insulin secretion for treating type II diabetes. European Patent Publication No. EP 1305301 discloses alpha-acyl & alpha-heteroatom-substituted benzene acetamide as glucokinase activators. International (PCT) Patent Publication No. WO2005/080359 discloses benzamide derivatives and their use as glucokinase activating agents. International (PCT) Patent Publication No. WO2005/080360 discloses benzamide derivatives as glucokinase activators. International (PCT) Patent Publication No. WO2005/121110 discloses heteroaryl benzamide derivatives for use as glucokinase activators in the treatment of diabetes. International (PCT) Patent Publication No. WO 2006/040528 discloses phenoxy benzamide compounds with utility in the treatment of type II diabetes and obesity. International (PCT) Patent Publication No. WO 2007/007042 describes heteroaryl benzamide derivatives for use as glucokinase activators in the treatment of diabetes.

However, the therapeutic potential of these compounds to treat diseases has not yet been proved and so there remains the need to develop newer medicines which are better or of comparable efficacy with the present treatment regimes, have lesser side effects and require a lower dosage regime We herein disclose novel compounds of general Formula (I) which are glucokinase activators and are useful for the prevention and treatment of diseases states mediated by Glucokinase (GK).

SUMMARY OF THE INVENTION

The present invention discloses certain disubstituted benzamide derivatives as defined by the general Formula (I) that are glucokinase activators and are useful for the prevention and treatment of disease states mediated by GK. The compounds of the present invention are useful in the treatment of human or animal body, by activation of GK. The compounds of this invention are therefore suitable for the prevention and treatment of disease states mediated by GK.

In one aspect there are provided disubstituted benzamide derivatives represented by the general Formula (I),

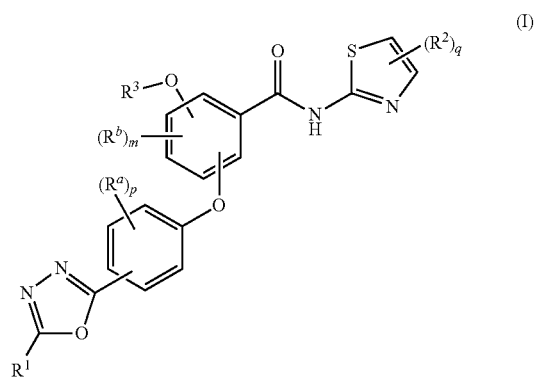

and their pharmaceutically acceptable salts, pharmaceutically acceptable solvates, enantiomers, diastereomers, prodrugs, metabolites and polymorphs.

In another aspect of the invention there are provided pharmaceutical compositions containing compounds of the general formula (I), their pharmaceutically acceptable salts, pharmaceutically acceptable solvates, enantiomers, diastereomers, prodrugs, metabolites and polymorphs in combination with suitable carriers, solvents, diluents and other media normally employed in preparing such compositions.

In another aspect there are provided the use of disubstituted benzamide derivatives of the present invention as GK activators, by administering a therapeutically effective and non-toxic amount of compounds of general Formula (I) or their pharmaceutically acceptable compositions to the mammals.

The details of one or more embodiments of the inventions are set forth in the description below. Other features, objects and advantages of the inventions will be apparent from the description.

DESCRIPTION OF THE INVENTION

Accordingly, the present invention relates to compounds of the general Formula (I),

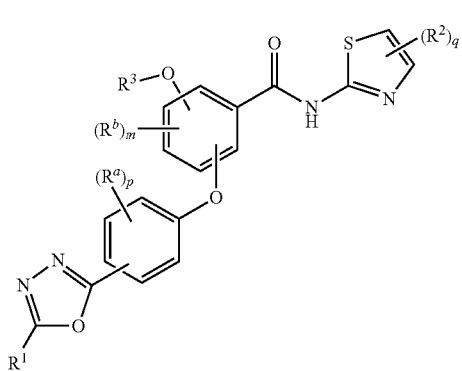

and their pharmaceutically acceptable salts, pharmaceutically acceptable solvates, enantiomers, diastereomers, prodrugs, metabolites and polymorphs, wherein
$R^1$ and $R^3$ are independently selected from halo, cyano, or optionally substituted groups selected from amino, $C_{1-6}$ alkyl, $C_{2-6}$ alkenyl, $C_{2-6}$ alkynyl, aryl, cycloalkyl, carbocycle, heterocycloalkyl, cycloalkyl($C_{1-6}$)alkyl, or heterocycloalkyl ($C_{1-6}$ alkyl, wherein any amino, alkyl, alkenyl, alkynyl, cycloalkyl, or heterocycloalkyl may be further substituted on available carbon atom with one to three substituent(s) independently selected from hydroxy, ($C_{1-4}$)alkoxy, halo, cyano, amino, ($C_{1-6}$)alkylamino, nitro, COO($C_{1-4}$)alkyl, S(O)$_n$, S(O)$_n$ NH$_2$, S(O)$_n$NH($C_{1-6}$)alkyl, C(O); or C(O)NH($C_{1-6}$) alkyl groups; n=0, 1, 2; m=0, 1, 2, 3; p=0, 1, 2, 3, 4; $R^2$ at each occurrence is independently selected from halo, amino, cyano, nitro, ($C_{1-4}$)alkyl, ($C_{2-6}$)alkenyl, ($C_{2-6}$)alkynyl, —(CH$_2$)$_n$COO($C_{1-4}$)alkyl, —(CH$_2$)$_n$COOH, S(O)$_n$, S(O)$_n$ NH$_2$, or S(O)$_n$NH($C_{1-6}$)alkyl, wherein any of the groups representing $R^2$ may be further substituted on available carbon atom with one to three substituent(s) independently selected from hydroxy, halo, cyano, nitro, or optionally substituted groups selected from ($C_{1-4}$)alkoxy, amino, ($C_{1-6}$)alkylamino, di($C_{1-6}$)alkylamino, S(O)$_n$, S(O)$_n$NH$_2$, or S(O)$_n$ NH($C_{1-6}$) alkyl, wherein n is defined as earlier and the substitutents on any of the substitutions defined above, if present, may be selected from those defined above; q=0-4; and $R^a$ & $R^b$ at each occurrence is independently selected from halo, cyano, nitro, hydroxyl, or optionally substituted groups selected from alkoxy, perfluoroalkoxy, amino, $C_{1-4}$alkyl, $C_{2-6}$ alkenyl, $C_{2-6}$ alkynyl, cycloalkyl, —(CH$_2$)$_n$ COO($C_{1-4}$)alkyl, or —(CH$_2$)$_n$ COOH, wherein any of the amino, alkyl, alkenyl, alkynyl, cycloalkyl or heterocycloalkyl groups as defined above may be further substituted on available carbon atom with one to three substituent(s) independently selected from hydroxy, ($C_{1-4}$)alkoxy, halo, cyano, amino, ($C_{1-6}$)alkylamino, nitro, COO($C_{1-4}$)alkyl, S(O)$_n$, S(O)$_n$ NH$_2$, S(O)$_n$NH($C_{1-6}$)alkyl, C(O); or C(O)NH($C_{1-6}$)alkyl groups.

In another embodiment there are provided compounds of the general Formula (I), wherein $R^1$ is independently selected from halo, cyano, or optionally substituted groups selected from amino, $C_{1-6}$ alkyl, $C_{2-6}$ alkenyl, $C_{2-6}$ alkynyl, aryl, cycloalkyl, carbocycle, heterocycloalkyl, cycloalkyl($C_{1-6}$)alkyl, or heterocycloallyl($C_{1-6}$)alkyl, wherein any amino, alkyl, alkenyl, alkynyl, cycloalkyl, or heterocycloalkyl may be further substituted on available carbon atom with one to three subsistent(s) independently selected from hydroxy, ($C_{1-4}$) alkoxy, halo, cyano, amino, ($C_{1-6}$)alkylamino, nitro, COO($C_{1-4}$)alkyl, S(O)$_n$, S(O)$_n$NH$_2$, S(O)$_n$NH($C_{1-6}$)alkyl, C(O); or C(O)NH($C_{1-6}$)alkyl groups; $R^2$ at each occurrence is selected from halo, amino, cyano, nitro, ($C_{1-4}$alkyl, ($C_{2-6}$) alkenyl, ($C_{2-6}$) alkynyl, —(CH$_2$)$_n$COO($C_{1-4}$)alkyl, —(CH$_2$)$_n$ COOH, S(O)$_n$, S(O)$_n$NH$_2$, or S(O)$_n$NH($C_{1-6}$)alkyl, wherein any of the groups representing $R^2$ may be further substituted on available carbon atom with one to three subsistent(s) independently selected from hydroxy, halo, cyano, nitro, or optionally substituted groups selected from ($C_{1-4}$)alkoxy, amino, ($C_{1-6}$)alkylamino, di($C_{1-6}$)alkylamino, COO($C_{1-4}$) alkyl, S(O)$_n$, S(O)$_n$NH$_2$, or S(O)$_n$NH($C_{1-6}$)alkyl; $R^a$ & $R^b$ at each occurrence is independently selected from halo, cyano, nitro, hydroxyl, or optionally substituted groups selected from alkoxy, perfluoroalkoxy, amino, $C_{1-4}$alkyl, $C_{2-6}$ alkenyl, $C_{2-6}$ alkynyl, cycloalkyl, —(CH$_2$)$_n$COO($C_{1-4}$)alkyl, or —(CH$_2$)$_n$ COOH, wherein any amino, alkyl, alkenyl, alkynyl, cycloalkyl, or heterocycloalkyl may be further substituted on available carbon atom with one to three subsistent(s) independently selected from hydroxy, ($C_{1-4}$)alkoxy, halo, cyano, amino, ($C_{1-6}$)alkylamino, nitro, COO($C_{1-4}$)alkyl, S(O)$_n$, S(O)$_n$ NH$_2$, S(O)$_n$NH($C_{1-6}$)alkyl, C(O); or C(O)NH($C_{1-6}$) alkyl groups; and $R^3$ is selected from, but not limited to:

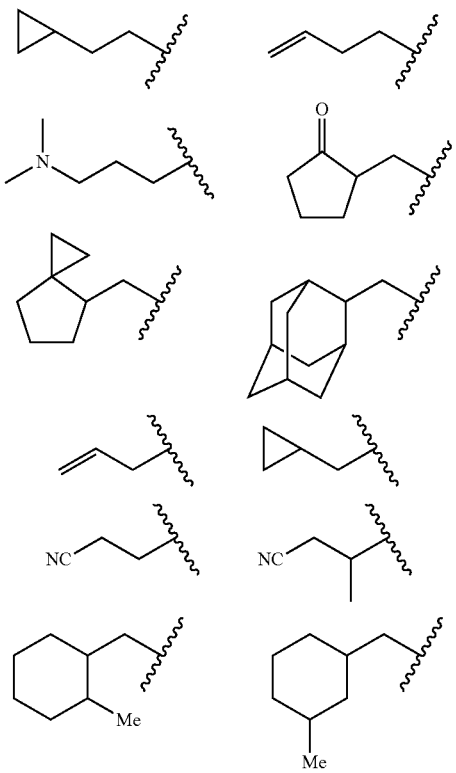

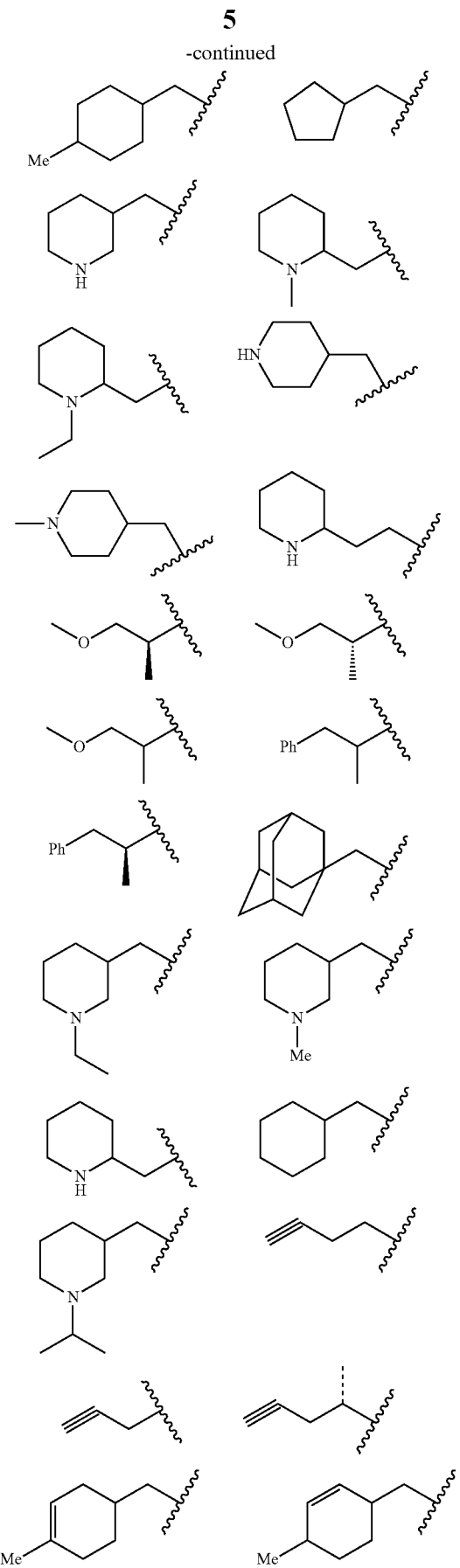
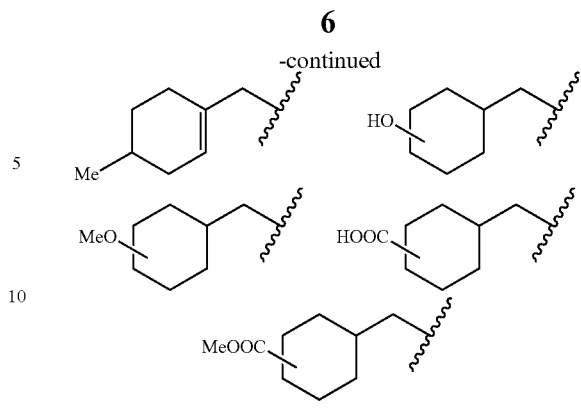

wherein m, n, p & q are as defined earlier and the substitutents on any of the substitutions defined above, if present, may be selected from those defined above.

In another embodiment, the groups, radicals described above may be selected from:

"Alkyl", as well as other groups having the prefix "alk", such as alkoxy and alkanoyl, means carbon chain which may either be linear or branched, and combinations thereof, unless the carbon chain is defined otherwise. Examples of alkyl group include but not limited to methyl, ethyl, propyl, isopropyl, butyl, sec-butyl, tert.-butyl, pentyl, hexyl etc. Where the specified number of carbon atoms permits e.g. from $C_{3-10}$, the term alkyl also includes cycloalkyl groups, and combinations of linear or branched alkyl chains combined with cycloalkyl structures. When no number of carbon to atoms is specified, $C_{1-6}$ is intended.

"Alkenyl" means carbon chains which contain at least one carbon-carbon double bond, and which may be linear or branched or combinations thereof, unless the carbon chain is defined otherwise. Examples of alkenyl include but not limited to vinyl, allyl, isopropenyl, hexenyl, pentenyl, heptenyl, 1-propenyl, 2-butenyl, 2-methyl-2-butenyl etc. Where the specified number of carbon atoms permits, e.g., from $C_{5-10}$, the term alkenyl also includes cycloalkenyl groups and combinations of linear, branched and cyclic structures. When no number of carbon atoms is specified, $C_{(2-6)}$ is intended.

"Alkynyl" means carbon chains which contain at least one carbon-carbon triple bond, and which may be linear or branched or combinations thereof. Examples of alkynyl include ethynyl, propargyl, 3-methyl-1-pentynyl etc. When no number of carbon atoms is specified, $C_{(2-6)}$ is intended.

As used herein, "carbocycle" or "carbocyclic residue" is intended to mean any stable monocyclic or bicyclic or tricyclic ring, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0] bicyclooctane, [4.3.0] bicyclononane, [4.4.0] bicyclodecane (decalin), [2.2.2] bicyclooctane, fluorenyl, phenyl, naphthyl, indanyl, adamantyl, or tetrahydronaphthyl (tetralin). In a broader perspetive, the term carbocycle is intended to include, wherever applicable, the groups representing cycloalkyl, phenyl and other saturated, partially saturated or aromatic residues;

"Cycloalkyl" is the subset of alkyl and means saturated carbocyclic ring having a specified number of carbon atoms, preferably 3-6 carbon atoms. Examples of cycloalkyl include cyclopropyl, cyclobutyl, cyclopentyl, cyclohexyl, cycloheptyl etc. A cycloalkyl group generally is monocyclic unless otherwise stated. Cycloalkyl groups are saturated unless and otherwise stated;

The "alkoxy" refers to a straight or branched chain alkoxides of the number of carbon atoms specified;

The term "alkylamino" refers to a straight or branched alkylamines of the number of carbon atoms specified;

"Aryl" means a mono- or polycyclic aromatic ring system containing carbon ring atoms. The preferred aryls are monocyclic or bicyclic 6-10 membered aromatic ring systems. Phenyl and naphthyl are preferred aryls;

"Heterocycle" and "heterocyclyl" refer to saturated or unsaturated non-aromatic rings or ring systems containing at least one heteroatom selected from O, S, N further including the oxidized forms of sulfur, namely SO & $SO_2$. Examples of heterocycles include tetrahydrofuran (THF), dihydrofuran, 1,4-dioxane, morpholine, 1,4-dithiane, piperazine, piperidine, 1,3-dioxo lane, imidazoline, imidazolidine, pyrrolidine, pyrroline, tetrahydropyran, dihydropyran, oxathiolant, dithiolane, 1,3-dioxane, 1,3-dithiane, oxathiane, thiomorpholine, and the like;

"Heteroaryl" means an aromatic or partially aromatic heterocycle that contains at least one ring heteroatom selected from O, S and N. Heteroaryls thus include heteroaryls fused to the other kinds of rings, such as aryls, cycloalkyls, and heterocycles that are not aromatic. Examples of heteroaryl groups include; pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzthiazolyl, benzothiadiazolyl, dihydrobenzofuranyl, indolinyl, pyridazinyl, indazolyl, isoindolyl, dihydrobenzothienyl, indolinyl, pyridazinyl, indazolyl, isoindolyl, dihydrobenzothienyl, indolizinyl, cinnolinyl, phthalazinyl, quinazolinyl, napthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 carbon atoms are included, forming 1-3 rings.

"Halogen" refers to fluorine, chlorine, bromine, iodine. Chlorine and fluorine are generally preferred;

Suitable groups and substituents on the groups may be selected from those described anywhere in the specification.

The term "substituted," as used herein, means that any one or more hydrogens on the designated atom is replaced with a selection from the indicated group, provided that the designated atom's normal valency is not exceeded, and that the substitution results in a stable compound. The term "substituted," as used herein, means that any one or more hydrogens on the designated atom is replaced with a selection from the indicated group, provided that the designated atom's normal valency is not exceeded, and that the substitution results in a stable compound.

Particularly useful compounds may be selected from but not limited to;

3-(But-3-enyloxy)-5-(4-(5-methyl-1,3,4-oxadiazol-2-yl)phenoxy)-N-(thiazol-2-yl)benzamide;
3-(But-3-enyloxy)-5-(4-(5-ethyl-1,3,4-oxadiazol-2-yl)phenoxy)-N-(thiazol-2-yl)benzamide;
3-(But-3-enyloxy)-5-(4-(5-isopropyl-1,3,4-oxadiazol-2-yl)phenoxy)-N-(thiazol-2-yl)benzamide;
3-(But-3-enyloxy)-5-(4-(5-cyclopropyl-1,3,4-oxadiazol-2-yl)phenoxy)-N-(thiazol-2-yl)benzamide;
3-(4-(5-Ccyclopropyl-1,3,4-oxadiazol-2-yl)phenoxy)-5-(2-cyclopropylethoxy)-N-(thiazol-2-yl)benzamide;
3-(2-Cyclopropylethoxy)-5-(4-(5-ethyl-1,3,4-oxadiazol-2-yl)phenoxy)-N-(thiazol-2-yl)benzamide;
3-(2-Cyclopropylethoxy)-5-(4-(5-isopropyl-1,3,4-oxadiazol-2-yl)phenoxy)-N-(thiazol-2-yl)benzamide;
3-(2-Cyclopropylethoxy)-5-(4-(5-isobutyl-1,3,4-oxadiazol-2-yl)phenoxy)-N-(thiazol-2-yl)benzamide;
3-(But-3-enyloxy)-5-(4-(5-isobutyl-1,3,4-oxadiazol-2-yl)phenoxy)-N-(thiazol-2-yl)benzamide
3-(Cyclohexylmethoxy)-5-(4-(5-isobutyl-1,3,4-oxadiazol-2-yl)phenoxy)-N-(thiazol-2-yl)benzamide;
3-(4-(5-isoButyl-1,3,4-oxadiazol-2-yl)phenoxy)-5-(piperidin-3-ylmethoxy)-N-(thiazol-2-yl)benzamide;
3-(1-Cyanopropan-2-yloxy)-5-(4-(5-cyclopropyl-1,3,4-oxadiazol-2-yl)phenoxy)-N-(thiazol-2-yl)benzamide;
3-(1-Cyanopropan-2-yloxy)-5-(4-(5-isopropyl-1,3,4-oxadiazol-2-yl)phenoxy)-N-(thiazol-2-yl)benzamide;
3-(1-Cyanopropan-2-yloxy)-5-(4-(5-ethyl-1,3,4-oxadiazol-2-yl)phenoxy)-N-(thiazol-2-yl)benzamide;
3-(4-(5-methyl-1,3,4-oxadiazol-2-yl)phenoxy)-5-((4(4-methylcyclohexyl)methoxy)-N-(thiazol-2-yl)benzamide;
3-(4-(5-Methyl-1,3,4-oxadiazol-2-yl)phenoxy)-5-((3-methylcyclohexyl)methoxy)-N-(thiazol-2-yl)benzamide;
3-(4-(5-methyl-1,3,4-oxadiazol-2-yl)phenoxy)-5-(piperidin-4-ylmethoxy)-N-(thiazol-2-yl)benzamide;
3-(4-(5-Methyl-1,3,4-oxadiazol-2-yl)phenoxy)-5-((1-methylpiperidin-4-yl)methoxy)-N-(thiazol-2-yl)benzamide;
3-(4-(5-methyl-1,3,4-oxadiazol-2-yl)phenoxy)-5-((1-methylpiperidin-3-yl)methoxy)-N-(thiazol-2-yl)benzamide;
3-(4-(5-Methyl-1,3,4-oxadiazol-2-yl)phenoxy)-5-(piperidin-3-ylmethoxy)-N-(thiazol-2-yl)benzamide;
3-(2-Cyanoethoxy)-5-(4-(5-methyl-1,3,4-oxadiazol-2-yl)phenoxy)-N-(thiazol-2-yl)benzamide;
3-(Cyclopropylmethoxy)-5-(4-(5-methyl-1,3,4-oxadiazol-2-yl)phenoxy)-N-(thiazol-2-yl)benzamide;
3-(Allyloxy)-5-(4-(5-methy-1,3,4-oxadiazol-2-yl)phenoxy)-N-(thiazol-2-yl)Benzamide;
3-(1-Cyanopropan-2-yloxy)-5-(4-(5-methyl-1,3,4-oxadiazol-2-yl)phenoxy)-N-(thiazol-2-yl)benzamide;
3-(4-(5-Methyl-1,3,4-oxadiazol-2-yl)phenoxy)-5-(spiro[2.4]heptan-5-ylmethoxy)-N-(thiazol-2-yl)benzamide;
3-(4-(5-Methyl-1,3,4-oxadiazol-2-yl)phenoxy)-5-((3-oxocyclopentyl)methoxy)-N-(thiazol-2-yl)benzamide;
3-(1-Methoxypropan-2-yloxy)-5-(4-(5-methyl-1,3,4-oxadiazol-2-yl)phenoxy)-N-(thiazol-2-yl)benzamide;
3-(1-Methoxybutan-2-yloxy)-5-(4-(5-methyl-1,3,4-oxadiazol-2-yl)phenoxy)-N-(thiazol-2-yl)benzamide;
3-(1-Methoxy-3-methylbutan-2-yloxy)-5-(4-(5-methyl-1,3,4-oxadiazol-2-yl)phenoxy)-N-(thiazol-2-yl)benzamide;
3-(4-(5-Ethyl-1,3,4-oxadiazol-2-yl)phenoxy)-5-(1-methoxypropan-2-yloxy)-N-(thiazol-2-yl)benzamide;
3-(4-(5-iso-Propy 1,3,4-oxadiazol-2-yl)phenoxy)-5-(1-methoxypropan-2-yloxy)-N-(thiazol-2-yl)benzamide;
3-(4-(5-Cyclopropyl-1,3,4-oxadiazol-2-yl)phenoxy)-5-(1-methoxypropan-2-yloxy)-N-(thiazol-2-yl)benzamide;
3-(4-(5-Cyclobutyl-1,3,4-oxadiazol-2-yl)phenoxy)-5-(1-methoxypropan-2-yloxy)-N-(thiazol-2-yl)benzamide;
3-(But-3-enyloxy)-5-(4-(5-methyl-1,3,4-oxadiazol-2-yl)phenoxy)-N-(thiazol-2-yl)benzamide
3-(2-Cyclopropylethoxy)-5-(4-(5-methyl-1,3,4-oxadiazol-2-yl)phenoxy)-N-(thiazol-2-yl)benzamide;
3-(3-(Dimethylamino)propoxy)-5-(4-(5-methyl-1,3,4-oxadiazol-2-yl)phenoxy)-N-(thiazol-2-yl)benzamide;
3-(Cyclohexylmethoxy)-5-(4-(5-methyl-1,3,4-oxadiazol-2-yl)phenoxy)-N-(thiazol-2-yl)benzamide;
3-(Cyclopentylmethoxy)-5-(4-(5-methyl-1,3,4-oxadiazol-2-yl)phenoxy)-N-(thiazol-2-yl)Benzamide;
3-(4-(5-iso-Propyl-1,3,4-oxadiazol-2-yl)phenoxy)-5-(piperidin-3-ylmethoxy)-N-(thiazol-2-yl)benzamide;
5-(1-Methoxypropan-2-yloxy)-2-(4-(5-methyl-1,3,4-oxadiazol-2-yl)phenoxy)-N-(thiazol-2-yl)benzamide;

2-(4-(5-Ethyl-1,3,4-oxadiazol-2-yl)phenoxy)-5-(1-methoxypropan-2-yloxy)-N-(thiazol-2-yl)benzamide;
2-(4-(5-iso-Propy 1,3,4-oxadiazol-2-yl)phenoxy)-5-(1-methoxypropan-2-yloxy)-N-(thiazol-2-yl)benzamide;
2-(4-(5-Cyclopropyl-1,3,4-oxadiazol-2-yl)phenoxy)-5-(1-methoxypropan-2-yloxy)-N-(thiazol-2-yl)benzamide;
2-(4-(5-iso-butyl-1,3,4-oxadiazol-2-yl)phenoxy)-5-(1-methoxypropan-2-yloxy)-N-(thiazol-2-yl)benzamide;
(S)-5-(1-Methoxypropan-2-yloxy)-2-(4-(5-methyl-1,3,4-oxadiazol-2-yl)phenoxy)-N-(thiazol-2-yl)benzamide;
(S)-3-(1-Methoxypropan-2-yloxy)-5-(4-(5-methyl-1,3,4-oxadiazol-2-yl)phenoxy)-N-(thiazol-2-yl)benzamide;
(S)-3-(1-Methoxypropan-2-yloxy)-5-(4-(5-methyl-1,3,4-oxadiazol-2-yl)phenoxy)-N-(thiazol-2-yl)benzamide;
(S)-3-(4-(5-Ethyl-1,3,4-oxadiazol-2-yl)phenoxy)-5-(1-methoxypropan-2-yloxy)-N-(thiazol-2-yl)benzamide;
(S)-3-(4-(5-iso-Propy-1,3,4-oxadiazol-2-yl)phenoxy)-5-(1-methoxypropan-2-yloxy)-N-(thiazol-2-yl)benzamide;
(S)-2-(4-(5-iso-Propyl-1,3,4-oxadiazol-2-yl)phenoxy)-4-(1-methoxypropan-2-yloxy)-N-(thiazol-2-yl)benzamide;
(S)-2-(4-(5-Ethyl-1,3,4-oxadiazol-2-yl)phenoxy)-4-(1-methoxypropan-2-yloxy)-N-(thiazol-2-yl)benzamide;
4-(1-Methoxypropan-2-yloxy)-2-(4-(5-methyl-1,3,4-oxadiazol-2-yl)phenoxy)-N-(4-methylthiazol-2-yl)benzamide;
N-(4-Chlorothiazol-2-yl)-4-(1-methoxypropan-2-yloxy)-2-(4-(5-methyl-1,3,4-oxadiazol-2-yl)phenoxy)benzamide;
N-(4-Fluorothiazol-2-yl)-4-(1-methoxypropan-2-yloxy)-2-(4-(5-methyl-1,3,4-oxadiazol-2-yl)phenoxy)benzamide;
4-(1-Methoxypropan-2-yloxy)-2-(4-(5-methyl-1,3,4-oxadiazol-2-yl)phenoxy)-N-(5-methylthiazol-2-yl)benzamide;
N-(5-Chlorothiazol-2-yl)-4-(1-methoxypropan-2-yloxy)-2-(4-(5-methyl-1,3,4-oxadiazol-2-yl)phenoxy)benzamide;
N-(5-Fluorothiazol-2-yl)-4-(1-methoxypropan-2-yloxy)-2-(4-(5-methyl-1,3,4-oxadiazol-2-yl)phenoxy)benzamide;
(S)—N-(5-Fluorothiazol-2-yl)-4-(1-methoxypropan-2-yloxy)-2-(4-(5-methyl-1,3,4-oxadiazol-2-yl)phenoxy)benzamide;
(S)—N-(5-Fluorothiazol-2-yl)-3-(1-methoxypropan-2-yloxy)-5-(4-(5-methyl-1,3,4-oxadiazol-2-yl)phenoxy)benzamide;
4-(Allyloxy)-N-(5-fluorothiazol-2-yl)-2-(4-(5-methyl-1,3,4-oxadiazol-2-yl)phenoxy)benzamide;
4-(But-3-enyloxy)-N-(5-fluorothiazol-2-yl)-2-(4-(5-methyl-1,3,4-oxadiazol-2-yl)phenoxy)benzamide;
4-(But-3-enyloxy)-2-(4-(5-ethyl-1,3,4-oxadiazol-2-yl)phenoxy)-N-(5-fluorothiazol-2-yl)benzamide;
4-(But-3-enyloxy)-N-(5-fluorothiazol-2-yl)-2-(4-(5-isopropyl-1,3,4-oxadiazol-2-yl)phenoxy)benzamide;
4-(But-3-enyloxy)-2-(4-(5-cyclopropyl-1,3,4-oxadiazol-2-yl)phenoxy)-N-(5-fluorothiazol-2-yl)benzamide;
4-(But-3-enyloxy)-N-(5-fluorothiazol-2-yl)-2-(4-(5-phenyl-1,3,4-oxadiazol-2-yl)phenoxy)benzamide;
4-(But-3-enyloxy)-2-(4-(5-cyano-1,3,4-oxadiazol-2-yl)phenoxy)-N-(5-fluorothiazol-2-yl)benzamide;
4-(But-3-enyloxy)-N-(5-fluorothiazol-2-yl)-2-(4-(5-(2-methoxyethyl)-1,3,4-oxadiazol-2-yl)phenoxy)benzamide;
4-(But-3-enyloxy)-N-(5-fluorothiazol-2-yl)-2-(4-(5-(2-hydroxyethyl)-1,3,4-oxadiazol-2-yl)phenoxy)benzamide;
3-(But-3-enyloxy)-N-(5-fluorothiazol-2-yl)-5-(4-(5-(2-hydroxyethyl)-1,3,4-oxadiazol-2-yl)phenoxy)benzamide;
3-(But-3-enyloxy)-N-(5-fluorothiazol-2-yl)-5-(4-(5-(2-methoxyethyl)-1,3,4-oxadiazol-2-yl)phenoxy)benzamide;
3-(2-Cyclopropylethoxy)-N-(5-fluorothiazol-2-yl)-5-(4-(5-(2-methoxyethyl)-1,3,4-oxadiazol-2-yl)phenoxy)benzamide;
3-(2-Cyclopropylethoxy)-N-(5-fluorothiazol-2-yl)-5-(4-(5-(2-hydroxyethyl)-1,3,4-oxadiazol-2-yl)phenoxy)benzamide;
4-((1-Ethylpiperidin-4-yl)methoxy)-2-(4-(5-methyl-1,3,4-oxadiazol-2-yl)phenoxy)-N-(5-methylthiazol-2-yl)benzamide;
4-((1-Ethylpiperidin-4-yl)methoxy)-N-(5-fluorothiazol-2-yl)-2-(4-(5-methyl-1,3,4-oxadiazol-2-yl)phenoxy)benzamide;
4-(1-Cyanopropan-2-yloxy)-N-(5-fluorothiazol-2-yl)-2-(4-(5-methyl-1,3,4-oxadiazol-2-yl)phenoxy)benzamide;
N-(5-Chlorothiazol-2-yl)-4-(1-cyanopropan-2-yloxy)-2-(4-(5-methyl-1,3,4-oxadiazol-2-yl)phenoxy)benzamide;
4-(1-Cyanopropan-2-yloxy)-2-(4-(5-methyl-1,3,4-oxadiazol-2-yl)phenoxy)-N-(4-methyl thiazol-2-yl)benzamide;
3-(But-3-enyloxy)-5-(3-(5-cyclopropyl-1,3,4-oxadiazol-2-yl)phenoxy)-N-(thiazol-2-yl)benzamide;
3-(3-(5-Cyclopropyl-1,3,4-oxadiazol-2-yl)phenoxy)-5-(1-methoxypropan-2-yloxy)-N-(thiazol-2-yl)benzamide;
(R)-3-(3-(5-Cyclopropyl-1,3,4-oxadiazol-2-yl)phenoxy)-5-(1-methoxypropan-2-yloxy)-N-(thiazol-2-yl)benzamide;
(R)-3-(1-methoxypropan-2-yloxy)-5-(3-(5-methyl-1,3,4-oxadiazol-2-yl)phenoxy)-N-(thiazol-2-yl)benzamide;
(R)-3-(3-(5-ethyl-1,3,4-oxadiazol-2-yl)phenoxy)-5-(1-methoxypropan-2-yloxy)-N-(thiazol-2-yl)benzamide;
(R)-3-(3-(5-isopropyl-1,3,4-oxadiazol-2-yl)phenoxy)-5-(1-methoxypropan-2-yloxy)-N-(thiazol-2-yl)benzamide;
(R)-3-(3-(5-cyano-1,3,4-oxadiazol-2-yl)phenoxy)-5-(1-methoxypropan-2-yloxy)-N-(thiazol-2-yl)benzamide;
(R)-3-(3-(5-cyano-1,3,4-oxadiazol-2-yl)phenoxy)-5-(1-methoxypropan-2-yloxy)-N-(5-methylthiazol-2-yl)benzamide;
(R)-3-(3-(5-Cyano-1,3,4-Oxadiazol-2-yl)phenoxy)-N-(5-fluorothiazol-2-yl)-5-(1-methoxypropan-2-yloxy)benzamide;
(R)—N-(5-Chlorothiazol-2-yl)-3-(3-(5-cyano-1,3,4-oxadiazol-2-yl)phenoxy)-5-(1-methoxypropan-2-yloxy)benzamide;
(R)—N-(5-Chlorothiazol-2-yl)-3-(1-methoxypropan-2-yloxy)-5-(3-(5-methyl-1,3,4-oxadiazol-2-yl)phenoxy)benzamide;
(R)—N-(5-Fluorothiazol-2-yl)-3-(1-methoxypropan-2-yloxy)-5-(3-(5-methyl-1,3,4-oxadiazol-2-yl)phenoxy)benzamide;
(R)-3-(3-(5-Ethyl-1,3,4-oxadiazol-2-yl)phenoxy)-N-(5-fluorothiazol-2-yl)-5-(1-methoxy propan-2-yloxy)benzamide;

or their pharmaceutically acceptable salts, pharmaceutically acceptable solvates, enantiomers, diastereomers, prodrugs, metabolites and polymorphs.

The novel compounds of the present invention may be prepared using the reactions and techniques described below, together with conventional techniques known to those skilled in the art of organic synthesis, or variations thereon as appreciated by those skilled in the art.

The reactions are performed in solvents appropriate to the reagents and materials employed and are suitable for the transformations being effected. Preferred methods include, but not limited to those described below, where all symbols are as defined earlier unless and otherwise defined below.

The compounds of the Formula (I) were prepared as described in schemes 1 and 2:

Dihydroxy methyl benzoate 2 was subjected to regiospecific nucleophilic displacement reaction (Scheme 1) with compound 3 in the presence of suitable base using appropriate solvent, most preferred being polar solvents like DMF, 1,4-dioxane to give compound 5. Alternatively, dihydroxy methyl benzoate 2 was subjected to standard Mitsunobu displacement reaction with suitable alcohol 4 to yield compound 5. Compound 5 after suitable nucleophilic displacement reaction with 4-substituted 1,3,4-oxadiazole arylhalide 6 in presence of suitable base in polar protic solvents to furnish compound 7 which was suitably hydrolyzed to yield acid 8.

The acid 8 (Scheme 2) was converted to its acid chloride with suitable chlorinating agents most preferred being oxalyl chloride or thionyl chloride followed by reaction with various suitable heterocyclic amines 9 to give compound (I). Alternatively, acid 8 was reacted with suitable differentially substituted heterocyclic amines 9 in the presence of N-(3-Dimethylaminopropyl)-N'-ethylcarbodiimide (EDCI) and 4-Dimethyl-aminopyridine (DMAP) in suitable chlorinated solvents, most preferably dichloromethane, chloroform, dichloroethane to furnish the compounds of the Formula (I).

known to those skilled in the art of organic synthesis, or variations thereon as appreciated by those skilled in the art.

Scheme 2:

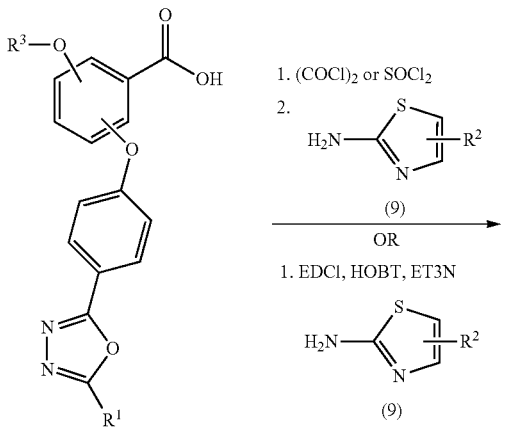

Scheme 1:

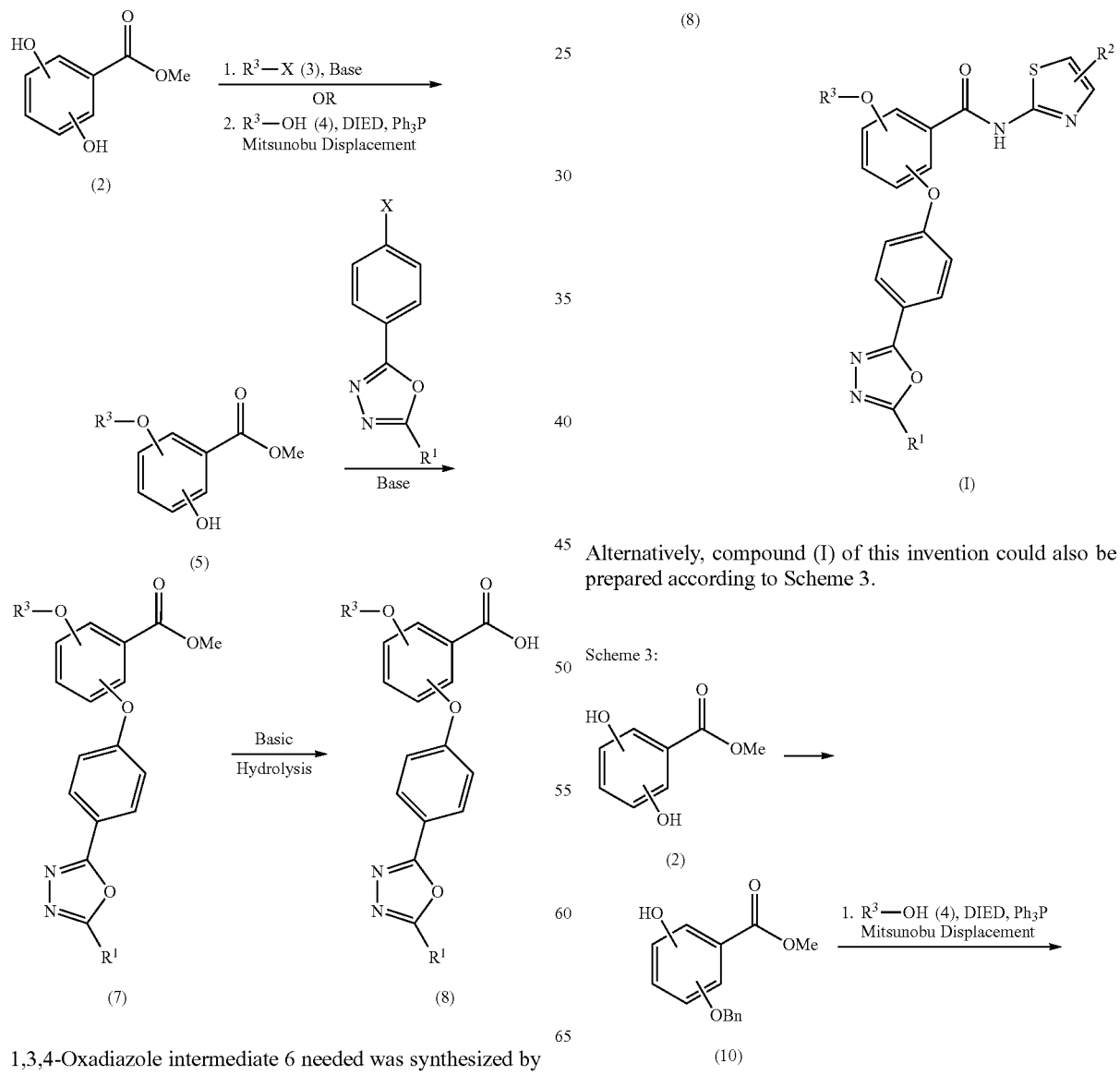

1,3,4-Oxadiazole intermediate 6 needed was synthesized by the known processes together with conventional techniques Alternatively, compound (I) of this invention could also be prepared according to Scheme 3.

Scheme 3:

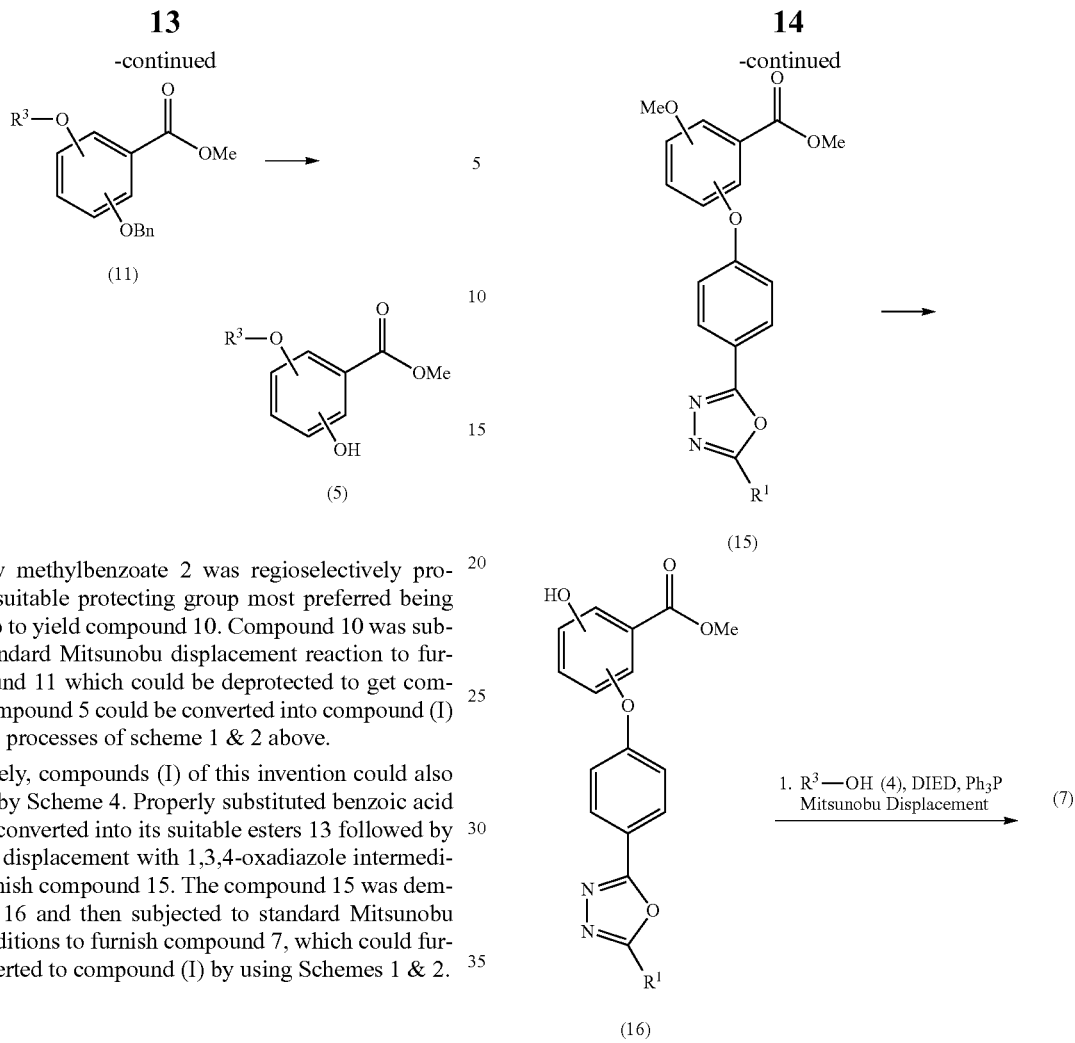

Dihydroxy methylbenzoate 2 was regioselectively protected with suitable protecting group most preferred being benzyl group to yield compound 10. Compound 10 was subjected to standard Mitsunobu displacement reaction to furnish compound 11 which could be deprotected to get compound 5. Compound 5 could be converted into compound (I) by following processes of scheme 1 & 2 above.

Alternatively, compounds (I) of this invention could also be prepared by Scheme 4. Properly substituted benzoic acid 12 could be converted into its suitable esters 13 followed by nucleophilic displacement with 1,3,4-oxadiazole intermediate 14 to furnish compound 15. The compound 15 was demethylated to 16 and then subjected to standard Mitsunobu reaction conditions to furnish compound 7, which could further be converted to compound (I) by using Schemes 1 & 2.

Scheme 4:

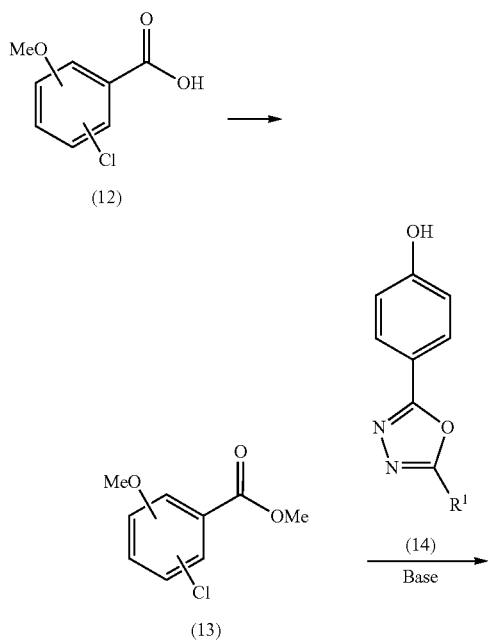

1,3,4-Oxadiazole intermediate 14 needed for nucleophilic displacement, was synthesized by the known processes together with conventional techniques known to those skilled in the art of organic synthesis, or variations thereon as appreciated by those skilled in the art.

Additionally, compounds (I) of the invention were also synthesized by following scheme 5. Suitable substituted halobenzadehyde 16 was subjected to nucleophilic substitution reaction with compound 10 by using base most preferred being sodium hydride, potassium carbonate or sodium carbonate in polar aprotic solvents like dimethyl formamide, tetrahydrofuran to furnish compound 17. Jones oxidation of 17 yielded acid 18. The acid 18 was converted to acid chloride by using chlorinating agent most preferred being either oxalyl chloride or thionyl chloride in chlorinated solvents most preferred being choloroform, dichloromethane or ethylene dichloride to give acid chloride. Acid chloride thus obtained was treated with acid hydrazide 19 in presence of base in solvents like chloroform, dichloromethane to obtain diamide 20. The compound 20 was cyclized using chlorinating agent preferred being thonyl chloride to get 1,3,4-oxadiazole 21 which was debenzylated under standard reaction condition to furnish the phenol 22. Mitsunobu reaction of the phenol 22 with suitable alcohol yielded compound 7. The compound 7 was converted to compound (I) by the processes described in Schemes 1 and 2.

Scheme 5:

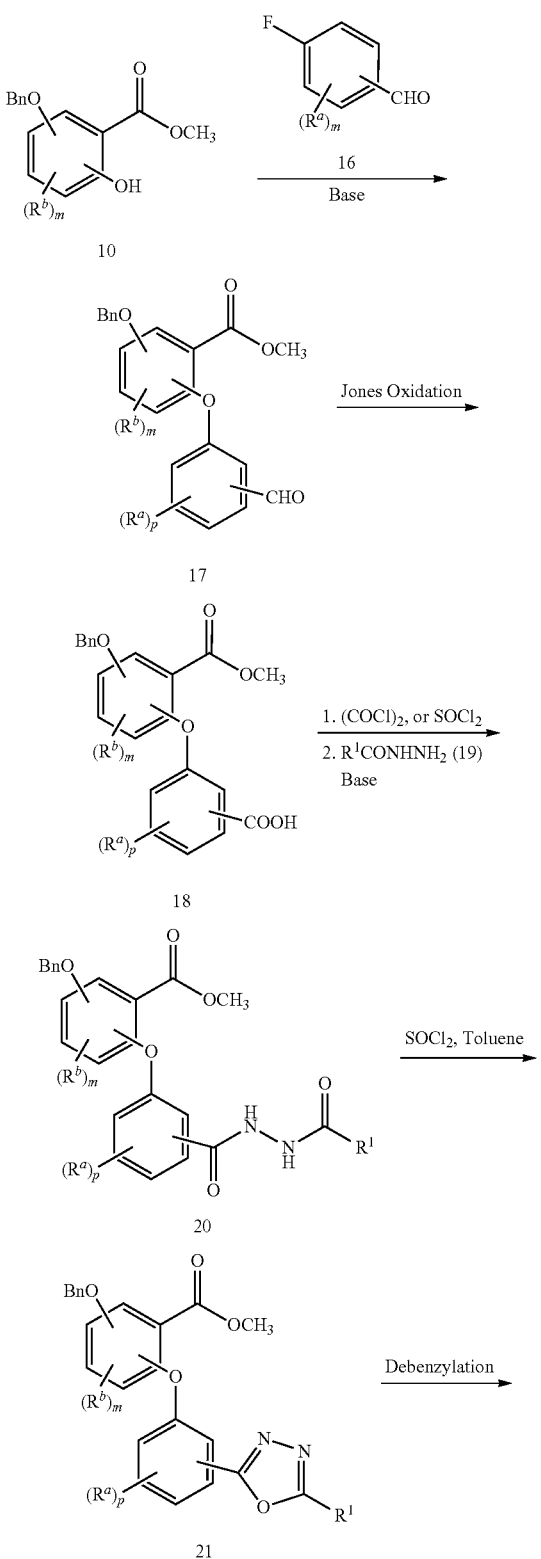

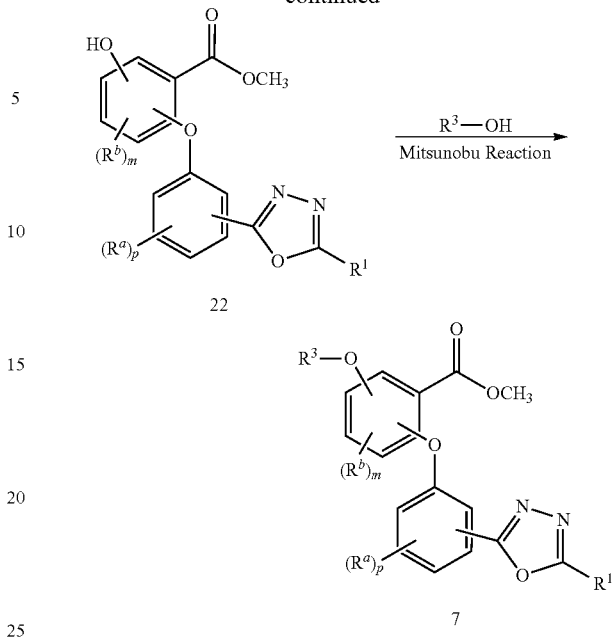

List of abbreviations used in the description of the preparation of the compounds of the present invention:
bs: broad singlet
n-BuLi: n-butyl lithium
$CDCl_3$: Deuterated chloroform
$CHCl_3$: Chloroform
d: doublet
dd: doublet of doublet
dt: doublet of triplet
DCM: Dichloromethane
DMAP: 4-(Dimethylamino) pyridine
DMF: N,N-Dimethyl formamide
DMSO: Dimethyl sulfoxide
EDCI: N-(3-Dimethylaminopropyl)-N'-ethylcarbodiimide
$Et_3N$: Triethyl amine
EtOAc: Ethyl acetate
EtOH: Ethanol
g: gram
HCl(g): Hydrogen chloride (gas)
HOBT: 1-Hydroxybenzotriazole
UPLC: High Performance Liquid Chromatography
$K_2CO_3$: Potassium carbonate
KI: Potassium iodide
KOH: Potassium hydroxide
$LiAlH_4$: Lithium Aluminum Hydride
LiHMDS: Lithium bis(trimethylsilyl)amide
MeOH: Methanol
m: multiplet
mmol: millimoles
mol: moles
mL: milliliter
MsCl: Methane sulfonyl chloride
MS: Mass spectrum
NaCN: Sodium cyanide
NaH: Sodium hydride
1H NMR: Proton nuclear magnetic resonance
Pet ether: Petroleum ether, boiling range (60-80° C.)
s: singlet
$SOCl_2$: Thionyl chloride
t: Triplet td: triplet of doublet
THF: Tetrahydrofuran
TLC: Thin layer chromatography
UPLC: Ultra Performance Liquid Chromatography The invention is further illustrated by the following examples, which are provided merely to be exemplary of the invention and do not limit the scope of the invention. Certain modifications and equivalents will be apparent to those skilled in the art and are intended to be included within the scope of the invention.

$^1$H NMR spectral data given in the examples (vide infra) are recorded using either a 300 MHz or a 400 MHz spectrometer and reported in δ scale. Until and otherwise mentioned the solvent used for NMR is $CDCl_3$ using tetramethyl silane as the internal standard.

The following examples were prepared according to the general Schemes described above, with suitable modifications/alterations as are well within the scope of a skilled person.

Example 1.1

3-(1-Methoxypropan-2-yloxy)-5-(4-(5-methyl-1,3,4-oxadiazol-2-yl)phenoxy)-N-(thiazol-2-yl)benzamide Oxalyl chloride (1.27 mL, 1.85 g, 14.53 mmole, 1.1 equiv.) was added slowly drop wise to a solution of 3-(1-methoxypropan-2-yloxy)-5-(4-(5-methyl-1,3,4-oxadiazol-2-yl)phenoxy)benzoic acid (Intermediate 1) (5.1 g, 13.27 mmol, 1 equiv.) in dry DCM (50 mL) and DMF (catalytic) under nitrogen at 0-5° C. The mixture was stirred for 3 h at 26° C. and solvents were evaporated in vacuo, the residue thus obtained was azeptroped once with dry DCM (20 mL) and then was dried under high vacuum to give the brown colored acid chloride, which was used without characterization. The acid chloride was dissolved in DCM (20 mL) under nitrogen atmosphere and cooled to 0° C., mixture of 2-Aminothiazole (1.45 g, 14.53 mmol, 1.1 eq.) and pyridine (2.132 g, 26.54 mmol, 2 equiv) in DCM (20 mL) was added slowly drop wise. The reaction was stirred 16 h at room temperature and it was diluted with commercially available DCM. Organic phase was washed with dil HCl (50 mL), saturated solution of $NaHCO_3$ (100 mL), water (2×100 mL), brine (100 mL), dried over $Na_2SO_4$, filtered and concentrated in vacuo to get the crude residue. This was chromatographed using silica gel as stationary phase and MeOH: $CHCl_3$ gradient as mobile phase to give 3-(1-methoxypropan-2-yloxy)-5-(4-(5-methyl-1,3,4-oxadiazol-2-yl)phenoxy)-N-(thiazol-2-yl)benzamide (3.2 g) as a white solid.

$^1$H NMR ($CDCl_3$, 400 MHz) δ ppm: 1.30 (d, J=6.4 Hz, 3 H), 2.62 (s, 3 H), 3.40 (s, 3 H), 3.48-3.52 (m, 1 H), 3.56-3.60 (m, 1 H), 4.58-4.63 (m, 1 H), 6.88 (t, J=2 Hz, 1 H), 6.99 (d, J=3.2 Hz, 1 H), 7.12 (d, J=8.4 Hz, 2 H); 7.20 (s, 1 H), 7.28 (s, 1 H), 7.35 (s, 1 H), 8.03 (d, J=8.4, 2 H), 10.65 (s, 1 H); ESI-MS m/z (relative intensities): 467.2 $(M+H)^+$ (100%), 489.15 $(M+Na)^+$ (85%); IR: (KBr $cm^{-1}$): 3389, 2963, 2928, 1614, 1448, 1263, 1088, 1024; UPLC purity: 96.6%, Ret.time: 4.243 min.

Intermediate 1: 3-(1-Methoxypropan-2-yloxy)-5-(4-(5-methyl-1,3,4-oxadiazol-2-yl)phenoxy)benzoic acid A solution of Methyl 3-(1-methoxypropan-2-yloxy)-5-(4-(5-methyl-1,3,4-oxadiazol-2-yl)phenoxy)benzoate (Intermediate 2) (6.8 g, 17.08 mmol, 1 equiv.) in a mixture of THF and methanol (70 mL of 1:1 ratio) was treated with a solution of sodium hydroxide (2 g, 51.25 mmol, 3 equiv.) in water (50 mL) and the reaction mixture was stirred for 1 h. The resulting solution was concentrated in vacuo to remove THF and methanol, diluted with water (50 mL), extracted with EtOAc. The aqueous phase was cooled and acidified with 0.1 N HCl and extracted with DCM, combined organic extracts washed with brine, dried over $Na_2SO_4$ and concentrated in vacuo to give 3-(1-methoxypropan-2-yloxy)-5-(4-(5-methyl-1,3,4-oxadiazol-2-yl)phenoxy)benzoic acid (5.1 g) as white solid.

$^1$H NMR ($CDCl_3$, 400 MHz) δ ppm: 1.30 (d, J=6.4 Hz, 3 H), 2.62 (s, 3 H), 3.40 (s, 3 H), 3.48-3.52 (m, 1 H), 3.56-3.60 (m, 1 H), 4.58-4.63 (m, 1 H), 6.88 (t, J=2.4 Hz, 1 H), 7.12 (d, J=8.4 Hz, 2 H), 7.26 (s, 1 H), 7.35 (s, 1 H), 7.47 (s, 1 H), 7.99 (d, J=8.4 Hz, 2 H), 9.86 (s, 1 H); ESI-MS m/z (relative intensities): 385.21 (M+H) (35%), 407.19 $(M+Na)^+$ (100%); IR: (KBr $cm^{-1}$): 3389, 2963, 2928, 1614, 1448, 1263, 1088, 1024; UPLC purity: 96.98%, Ret.time: 4.29 min.

Intermediate 2: Methyl 3-(1-methoxypropan-2-yloxy)-5-(4-(5-methyl-1,3,4-oxadiazol-2-yl)phenoxy)benzoate To a stirred suspension of Methyl 3-hydroxy-5-(1-methoxypropan-2-yloxy)benzoate (Intermediate 3) (7.88 g, 32.84 mmol, 1.3 equiv.), N,N-dimethylglycine hydrochloride (1 g, 7.69 mmol. 30 mole %), Cesium carbonate (16.5 g, 50.52 mmol, 2 equiv.), copper (II) iodide (0.488 g, 2.56 mmol, 0.1 mole %) in dry dioxane was added 2-(4-iodophenyl)-5-methyl-1,3,4-oxadiazole (7.2 g, 25.26 mmol, 1 equiv.) under nitrogen. The reaction mixture was heated up to reflux at 100° C. for 24 h. The reaction mixture was cooled, quenched with water and extracted with DCM. Combined organic washings were washed with water, brine, dried over $Na_2SO_4$, filtered and concentrated in vacuo to get the crude product. The crude product was purified by column chromatography using silica gel as stationary phase and EtOAc: petroleum ether as mobile phase to furnish the product (6.8 g) as thick liquid.

$^1$H NMR ($CDCl_3$, 400 MHz) δ ppm: 1.30 (d, J=6.4 Hz, 3 H), 2.61 (s, 3 H), 3.38 (s, 3 H), 3.48-3.51 (m, 1 H), 3.54-3.60 (m, 1 H), 3.89 (s, 3 H), 4.57-4.62 (m, 1 H), 6.84 (t, J=2 Hz, 1 H), 7.09 (d, J=8.4 Hz, 1 H), 7.30 (s, 1 H), 7.43 (s, 1 H), 8.01 (d, J=8.4 Hz, 2 H); ESI-MS m/z (relative intensities): 399.11 $(M+H)^+$ (100%), 421.09 $(M+Na)^+$ (30%).

Intermediate 3: Methyl 3-hydroxy-5-(1-methoxypropan-2-yloxy)benzoate

To a solution of Methyl 3-(benzyloxy)-5-(1-methoxypropan-2-yloxy)benzoate (Intermediate 4) (11.2 g, 33.93 mmol) in methanol (150 mL) was added Pd/C (1.12°g, 10% w/w), and the resulting suspension was stirred at ambient temperature overnight under hydrogen atmosphere. The catalyst was filtered off and washed with methanol and THF, and filtrate was evaporated to give methyl 3-hydroxy-5-(1-methoxypropan-2-yloxy)benzoate (8 g, 33.33 mmol, 98%) as white solid.

$^1$H NMR ($CDCl_3$, 400 MHz) δ ppm: 1.30 (d, J=6.4 Hz, 3 H), 3.42 (s, 3 H), 3.48-3.52 (m, 1 H), 3.57-3.61 (m, 1 H), 3.88 (s, 3 H), 4.54-4.59 (m, 1 H), 5.91 (bs, 1 H), 6.63 (t, J=2 Hz, 1 H), 7.10 (dd, J=1.6, 2 Hz, 1 H), 7.15 (dd, J=1.6, 2 Hz 1 H); UPLC purity: 95.40%, Ret. time: 3.38 min.

Intermediate 4: Methyl 3-(benzyloxy)-5-(1-methoxypropan-2-yloxy)benzoate

To a stirred suspension of Methyl-3-hydroxy-5-benzyloxy benzoate (Intermediate 5) (9 g, 34.83 mmol, 1 equiv.) and triphenyl phosphine (18.3 g, 69.76 mmol, 2 equiv.) in dry THF (100 mL), under nitrogen was added 1-methoxy-2-propanol (4.14 g, 46.04 mmol, 1.32 equiv.) at 26° C. The reaction was cooled to 0° C.-5° C. and (Diisopropylazodocarboxylate) DIAD (10.5 g, 52.32 mmol, 1.5 equiv.) was added. The reaction mixture was stirred overnight at ambeint temperature. Most of the organic solvent was removed in vacuo and diluted the residue with the DCM (50 mL), passed through bad of silica gel using EtOAc: Pet ether as eluent. The desired product was eluted at 1:9 EtOAc:petroleum ether. Methyl 3-(benzyloxy)-5-(1-methoxypropan-2-yloxy)benzoate was obtained as thick liquid (11.2 g)

$^1$H NMR (CDCl$_3$, 400 MHz) δ ppm: 1.30 (d, J=6.4 Hz, 3 H), 3.40 (s, 3 H), 3.46-3.50 (m, 1 H), 3.55-3.59 (m, 1 H), 3.89 (s, 3 H), 4.55-4.59 (m, 1 H), 5.29 (s, 2 H), 6.76 (t, J=2.4 Hz, 1 H), 7.23-7.22 (m, 1 H), 7.27-7.26 (m, 1 H), 7.33-7.31 (m, 1 H), 7.39-7.45 (m, 2 H), 7.44-7.40 (m, 2 H); ESI-MS m/z (relative intensities): 331.2 (M+H)$^+$ (60%), 352.9 (M+Na)$^+$ (100%); UPLC Purity: 94.66%, Ret.time: 5.25 min.

Intermediate 5: Methyl-3-hydroxy-5-benzyloxy benzoate

To a stirred solution of Methyl 3,5-dihydroxy benzoate [CAS No. 2150-44-9] (20 g, 119.04, 1 equiv.) in dry DMF (150 mL) was added potassium carbonate (25 g, 180.1 mmol, 1.52 equiv.), and the suspension stirred at ambient temperature under nitrogen. To this was added benzyl bromide (28.9 g, 169.05 mmol, 1.42 equiv.) and the reaction mixture stirred overnight at ambient temperature. It was then quenched with ammonium chloride solution followed by water. The aqueous suspension was extracted with EtOAc. The combined extracts were washed with water, brine, dried over Na$_2$SO$_4$, and filtered through cotton, concentrated under reduced pressure to get the thick liquid residue. The crude product was purified by column chromatography using Silica gel as stationary phase and EtOAc: Pet ether Gradient as a mobile phase. Methyl-3-hydroxy-5-benzyloxy benzoate was eluted at 1:4 EtOAc:Pet ether. Pure white solid (9 g, 34.83 mmol, 31%) was obtained after column chromatography.

$^1$H NMR (DMSO-d$_6$, 400 MHz) δ ppm: 3.81 (s, 3 H), 5.09 (s, 2 H), 6.64 (t, J=2.4 Hz, 1 H), 7.00-6.96 (m, 2 H), 7.33-7.29 (m, 1 H), 7.38-7.36 (m, 2 H), 7.44-7.39 (m, 2 H), 9.86 (s, 1 H); ESI-MS m/z (relative intensities): 259 (M+H)$^+$, (35%), 281 (M+Na)$^+$ (100%)

UPLC: 96.98%, Ret. Time: 4.29 min.

Following examples were prepared by using the similar procedure as that of Example 1.1 with suitable modifications/amendments as may be required and which are within the scope of a skilled person.

Example 1.2

3-(But-3-enyloxy)-5-(4-(5-methyl-1,3,4-oxadiazol-2-yl)phenoxy)-N-(thiazol-2-yl)benzamide $^1$H NMR (DMSO-d$_6$, 400 MHz) δ ppm: 2.51-2.53 (m, 2 H), 2.56 (s, 3 H), 4.14 (t, J=6.4 Hz, 2 H), 5.08 (d, J=10.4 Hz, 1 H), 5.20 (dd, J=17.2, 1.6 Hz, 1 H), 5.83-5.89 (m, 1 H), 6.96 (t, J=2 Hz, 1 H), 7.23 (d, J=8.8 Hz, 2 H), 7.28 (d, J=3.6 Hz, 1 H), 7.38 (d, J=1.6 Hz, 1 H), 7.55 (d, J=3.6 Hz, 1 H), 7.57-7.59 (m, 1 H), 8.00 (d, J=8.8 Hz, 2 H), 12.68 (s, 1 H); UPLC purity: 95.72%, Ret.time: 4.73 min.

Example 1.3

2-(1-Methoxypropan-2-yloxy)-5-(4-(5-methyl-1,3,4-oxadiazol-2-yl)phenoxy)-N-(thiazol-2-yl)benzamide $^1$H NMR (DMSO-d$_6$, 400 MHz) δ ppm: 1.37 (d, J=6.4 Hz, 3 H), 2.56 (s, 3 H), 3.35 (s, 3 H), 3.59-3.62 (m, 2 H), 4.85-4.89 (m, 1 H), 7.17 (d, J=8.8 Hz, 2 H), 7.29 (d, J=3.6 Hz, 1 H), 7.41 (d, J=2.8 Hz, 2 H), 7.54 (d, J=3.6 Hz, 1 H), 7.58 (d, J=2 Hz, 1 H), 7.96 (d, J=8.8 Hz, 2 H), 11.74 (s, 1 H); ESI-MS m/z (relative intensities): 467 (M+H)$^+$ (100%) 490.0 (M+Na)$^+$ (10%); UPLC purity: 98.79%, Ret.time: 4.61 min.

Example 1.4

3-(1-Cyclopropylethoxy)-5-(4-(5-methyl-1,3,4-oxadiazol-2-yl)phenoxy)-N-(thiazol-2-yl)benzamide $^1$H NMR (CDCl$_3$, 400 MHz) δ ppm: 0.28-0.31 (m, 1 H), 0.36-0.39 (m, 1 H), 0.56-0.59 (m, 2 H), 1.11-1.13 (m, 1 H), 1.34 (d, J=6.4 Hz, 3 H), 2.61 (s, 3 H), 3.86-3.92 (m, 1 H), 6.28 (s, 1 H), 6.99 (d, J=3.2 Hz, 1 H), 7.11 (d, J=8.4 Hz, 2 H), 7.17 (s, 1 H), 7.28 (s, 1 H), 8.32 (d, J=3.8 Hz, 1 H), 8.17 (d, J=8.4 Hz, 2 H), 10.97 (s, 1 H); UPLC Purity: 87.72%, Ret.time.: 4.871 min.

Example 1.5

3-(Cyclopropylmethoxy)-5-(4-(5-methyl-1,3,4-oxadiazol-2-yl)phenoxy)-N-(thiazol-2-yl)benzamide $^1$H NMR (CDCl$_3$, 400 MHz) δ ppm: 0.33-0.37 (m, 2 H), 0.64-0.68 (m, 2 H), 1.30-1.36 (m, 1 H), 2.61 (s, 3 H), 3.84 (d, J=6.8 Hz, 2 H), 6.84 (d, J=2.0 Hz, 1 H), 7.00 (d, J=3.6 Hz, 1 H), 7.12 (d, J=8.8 Hz, 2 H), 7.18 (d, J=1.6 Hz, 1 H), 7.27 (d, J=2.0 Hz, 1 H), 7.35 (d, J=3.6 Hz, 1 H), 8.02 (d, J=8.8 Hz, 2 H), 10.59 (s, 1 H); UPLC Purity: 99.25%, Ret.time.: 4.651 min.

Example 1.6

3-(4-(5-Methyl-1,3,4-oxadiazol-2-yl)phenoxy)-5-(spiro[2.4]heptan-5-ylmethoxy)-N-(thiazol-2-yl)benzamide $^1$H NMR (CDCl$_3$, 400 MHz) δ ppm: 0.42-0.46 (m, 4 H), 1.28-1.37 (m, 2 H), 1.44-1.47 (m, 2 H), 1.71-1.75 (m, 1 H), 1.95-2.00 (m, 1 H), 2.57-2.59 (m, 1 H), 2.61 (s, 3 H), 3.90-3.97 (m, 2 H), 6.84 (s, 1 H), 7.00 (d, J=3.6 Hz, 1 H), 7.12 (d, J=8.8 Hz, 2 H), 7.19 (s, 1 H), 7.27 (s, 1 H), 7.38 (d, J=3.6 Hz, 1 H), 8.02 (d, J=8.4 Hz, 2 H); UPLC Purity: 93.21%, Ret.time.: 5.746 min.

Example 1.7

3-(3-Methoxybutoxy)-5-(4-(5-methyl-1,3,4-oxadiazol-2-yl)phenoxy)-N-(thiazol-2-yl)benzamide $^1$H NMR (CDCl$_3$, 400 MHz) δ ppm: 1.21 (d, J=5.6 Hz, 3 H), 1.86-2.01 (m, 2 H), 2.60 (s, 3 H), 3.33 (s, 3 H), 3.53-3.55 (m, 1 H), 4.09-4.14 (m, 2 H), 6.85 (s, 1 H), 7.00 (s, 1 H), 7.12 (d, J=8.8 Hz, 2 H), 7.21 (s, 1 H), 7.33 (s, 1 H), 7.35 (s, 1 H), 8.02 (d, J=8.8 Hz, 2 H); ESI-MS m/z (relative intensities): 481.07 (M+H)$^+$, (90%), 503.08 (M+Na)$^+$ (70%); UPLC Purity: 93.40%, Ret.time: 4.476 min.

Example 1.8

3-(3-Methoxybutoxy)-5-(4-(5-methyl-1,3,4-oxadiazol-2-yl)phenoxy)-N-(5-methylthiazol-2-yl)benzamide $^1$H NMR (CDCl$_3$, 400 MHz) δ ppm: 1.20 (d, J=6.0 Hz, 3 H), 1.89-1.98 (m, 2 H), 2.39 (s, 3 H), 2.61 (s, 3 H), 3.32 (s, 3

H), 3.52-3.56 (m, 1 H), 4.05-4.05 (m, 2 H), 6.83 (s, 1 H), 6.96 (s, 1 H), 7.11 (d, J=8.8 Hz, 2 H), 7.19 (s, 1 H), 7.31 (s, 1 H), 8.01 (d, J=8.4 Hz, 2 H); ESI-MS m/z (relative intensities): 495.14 (M+H)$^+$ (100%), 517.14 (M+Na)$^+$ (90%) (+ve mode); UPLC Purity: 98:60%, Ret.time: 4.669 min.

Example 1.9

3-(4-(5-Methyl-1,3,4-oxadiazol-2-yl)phenoxy)-5-(admantanemethoxy)-N-(thiazol-2-yl)benzamide $^1$H NMR (CDCl$_3$, 400 MHz) δ ppm: 1.58-1.63 (m, 6 H), 1.64-1.67 (m, 4 H), 1.70-1.78 (m, 3 H), 2.02-2.08 (m, 3 H), 2.61 (s, 3 H), 3.54 (s, 2 H), 6.85 (d, J=2 Hz, 1 H), 7.12 (d, J=8.8 Hz, 2 H), 7.20 (t, J=1.6 Hz, 1 H), 7.32 (t, J=2 Hz, 1 H), 7.40 (d, J=3.2 Hz, 1 H), 8.02 (d, J=8.8 Hz, 2 H); UPLC Purity: 97.50%, Ret.time: 6.454 min. Certain compounds of formula (I) of the present invention was also synthesized by following Scheme 5 to obtain ester (7). Thus, the ester (7) obtained was hydrolyzed and coupled with substituted or unsubstituted thiazole amines. Following examples were synthesized according to schemes 5 and 2.

Example 2.1

(S)-3-(1-Methoxypropan-2-yloxy)-5-(4-(5-methyl-1, 3,4-oxadiazol-2-yl)phenoxy)-N-(thiazol-2-yl)benzamide To a stirring solution of (8)-3-[(1-methoxypropan-2-yl) oxy]-5-[4-(5-methyl-1,3,4-oxadiazol-2-yl)phenoxy]benzoic acid (Intermediate 6) (4.5 g, 11.7 mmol, 1 equiv.) in dry DCM (80 mL) under nitrogen atmosphere was added N,N'-Dimethylaminopyridine (DMAP) (1.43 g, 11.7 mmol, 1 equiv.) followed by EDCI.HCl (4.48 g, 23.4 mmol, 2 equiv.) at 0° C. The reaction mixture was stirred for 5-10 minutes, and 2-Aminothiazole (1.29 g, 12.87 mmol, 1.1 equiv.) was added at 0° C. The stirring was continued for 16 h. After completion, reaction mixture was diluted with DCM and washed with dil HCl, brine, saturated sodium bicarbonate, and dried over anhydrous sodium sulphate, filtered and concentrated to give the title compound. It was purified by column chromatography to obtain pure compound (3.8 g) as white solid.

$^1$H NMR (CDCl$_3$, 400 MHz) δ ppm: 1.33 (d, J=6.4 Hz, 3 H), 2.62 (s, 3 H), 3.40 (s, 3 H), 3.49-3.52 (m, 1 H), 3.56-3.60 (m, 1 H), 4.58-4.62 (m, 1 H), 6.88 (t, J=2.4 Hz, 1 H), 7.00 (d, J=3.6 Hz, 1 H), 7.13 (d, J=8.8 Hz, 2 H), 7.17 (t, J=1.6 Hz, 1 H), 7.32 (d, J=1.6 Hz, 1 H), 7.39 (d, J=3.6 Hz, 1 H), 8.02 (d, J=8.8 Hz, 2 H), 10.32 (s, 1 H);

ESI-MS: m/z (relative intensities): 467.19 (M+H)$^+$ (100%); UPLC Purity: 96.97%, Ret.tim.: 4.24 min.

Intermediate 6: (S)-3-[(1-methoxypropan-2-yl)oxy]-5-[4-(5-methyl-1,3,4-oxadiazol-2-yl)phenoxy]benzoic acid Triphenyl phosphine (21 g, 80 mmol, 2.8 equiv.) was added to a stirring solution of Methyl 3-hydroxy-5-(4-(5-methyl-1, 3,4-oxadiazol-2-yl)phenoxy)benzoate (Intermediate 7) (9.3 g, 28.52 mmol, 1 equiv.) in toluene (100 mL) under nitrogen atmosphere at room temperature. The mixture was heated to 90° C. for 30 min. A mixture of Diisopropylazadicarboxylate (DIAD) (11.52 g, 57 mmol, 2 equiv.) and (R)-(–)-1-Methoxypropan-2-ol (3.8 g, 42.8 mmol, 1.5 equiv.) in toluenene (50 mL) was added to the above reaction mixture at 90° C. and the reaction mixture was stirred for 3 h at 100° C. The completion of the reaction was monitored by TLC. After completion, the reaction mixture was concentrated under vacuum and purified by column chromatography to get (5)-Methyl 3-[(1-methoxypropan-2-yl)oxy]-5-[4-(5-methyl-1,3,4-oxadiazol-2-yl)phenoxy]benzoate (Intermediate 8) as thick liquid (27 g). Sodium hydroxide (3.43 g, 85.92 mmol, 3 equiv.) in water (55 mL) was added to a stirring solution of (9-Methyl 3-[(1-methoxypropan-2-yl)oxy]-5-[4-(5-methyl-1,3,4-oxadiazol-2-yl)phenoxy]benzoate (crude) (Intermediate 8) in methanol (110 mL) in round bottomed flask. The reaction mixture was stirred at room temperature for 2 h. The reaction was monitored by TLC. After completion, methanol was removed under vacuum and water was added. The reaction mixture was filtered. Filtrate was washed with ethyl acetate. The aqueous layer was acidified and extracted with DCM twice. The combined organic layer was washed with water, brine and dried over anhydrous sodium sulphate, filtered and concentrated in vacuum to furnish title acid as thick liquid (9.5 g).

$^1$H NMR (CDCl$_3$, 400 MHz) δ ppm: 1.33 (d, J=6.4 Hz, 3 H), 2.63 (s, 3 H), 3.41 (s, 3 H), 3.51-3.53 (m, 1 H), 3.57-3.61 (m, 1 H), 4.59-4.63 (m, 1 H), 6.88 (t, J=2 Hz, 1 H), 7.10 (d, J=8.8 Hz, 2 H), 7.35 (s, 1 H), 7.48 (s, 1 H), 8.01 (d, J=8.8 Hz, 2 H); ESI-MS m/z (relative intensities): 385.2 (M+H)$^+$ (100%), 407.19 (M+Na)$^+$ (100%); UPLC Purity: 97.91%; Ret.time.: 3.79 min.

Intermediate 7: Methyl 3-hydroxy-5-(4-(5-methyl-1, 3,4-oxadiazol-2-yl)phenoxy)benzoate Methyl 3-(benzyloxy)-5-(4-(5-methyl-1,3,4-oxadiazol-2-yl)phenoxy)benzoate (28 g, 72.1 mmol, 1 equiv.) (Intermediate 9) was debenzylated in acetic acid using 10% Pd/C (5.6 g) at 60 PSI in hydrogenation apparatus. After complete reaction, the reaction mixture was poured on ice and the solid obtained was filtered through Buckner funnel. The solid was washed with water and air-dried to furnish the title compound (18 g).

$^1$H NMR (CDCl$_3$, 400 MHz) δ ppm: 2.56 (s, 3 H), 3.79 (s, 3 H), 6.76 (t, J=2.4 Hz, 1 H), 6.99 (s, 1 H), 7.19 (d, J=8.8 Hz, 2 H), 7.22 (s, 1 H), 7.99 (d, J=8.8 Hz, 2 H), 10.24 (bs, 1 H); ESI-MS m/z (relative intensities): 327.17 (M+H)$^+$ (90%), 349.14 (M+Na)$^+$ (100%); UPLC Purity: 97.40, Ret.time.: 3.661 min.

Intermediate 9: Methyl 3-(benzyloxy)-5-(4-(5-methyl-1,3,4-oxadiazol-2-yl)phenoxy)benzoate To a stirring mixture of Methyl 3-(4-(2-acetylhydrazinecarbonyl)phenoxy)-5-(benzyloxy)benzoate (Intermediate 10) (32 g, 73.7 mmol, 1 equiv.) in toluene in a single necked round bottomed flask fitted with reflux condenser and anhydrous CaCl$_2$ guard tube, thonyl chloride (10.5 g, 88.4 mmol, 1.2 equiv.) was added carefully. The reaction mixture was refluxed until the reaction was complete. After completion, the reaction mixture was poured onto ice and extracted twice with ethyl acetate. The combined organic extracts was washed with brine and dried over anhydrous sodium sulphate, filtered and concentrated under vacuum to give the title compound as yellow solid product (30 g).

$^1$H NMR (CDCl$_3$, 400 MHz) δ ppm: 2.61 (s, 3 H), 3.90 (s, 3 H), 5.09 (s, 2 H), 6.88 (t, J=2.4 Hz, 1 H), 7.08 (d, J=8.8 Hz, 2 H), 7.33 (s, 1 H), 7.43-7.34 (m, 5 H), 7.49 (s, 1 H), 8.00 (d, J=8.8 Hz, 2 H); ESI-MS m/z (relative intensities): 417.18 (M+H)$^+$ (100%), 439.17 (M+Na)$^+$ (80%); UPLC Purity: 93.98%, Ret.time: 5.218 min.

Intermediate 10: Methyl 3-(4-(2-acetylhydrazinecarbonyl)phenoxy)-5-(benzyloxy)benzoate To a stirring solution of 4-[3-(benzyloxy)-5-(methoxycarbonyl)phenoxy]benzoic acid (Intermediate 11) (34 g, 82.87 mmol, 1 equiv) in dry DCM (50 mL), DMF (1.5 mL, catalytic) was added followed by oxalyl chloride (20.1 g, 158.7 mmol, 2 equiv.) dropwise at 0-5° C. The reaction mixture was stirred at room temperature for 2 h. After 2 h, a mixture of acetic hydrazide (8.8 g, 119 mmol, 1.5 equiv.) and dry pyridine (12.4 mL, 158.7 mmol, 2 equiv.) in dry DCM (50 mL) was added to the above prepared acid chloride at 0° C. The reaction mixture was allowed to warm to room temperature and stirred for 15 min. The reaction was monitored by TLC. After completion, the reaction mixture was diluted with dil. HCl and extracted with DCM. The organic layer was washed with water, brine and dried over sodium sulphate and concentrated to afford white solid. (32 g).

$^1$H NMR (CDCl$_3$, 400 MHz) δ ppm: 2.12 (s, 3 H), 3.88 (s, 3 H), 5.08 (s, 2 H), 6.85 (t, J=2.4 Hz, 1 H), 6.99 (d, J=8.8 Hz, 2 H), 7.29 (s, 1 H), 7.33-7.42 (m, 5 H), 7.48 (s, 1 H), 7.80 (d, J=8.4 Hz, 2 H), 8.81 (d, J=5.6 Hz, 1 H), 9.15 (J=5.2 Hz, 1 H); ESI-MS m/z (relative intensities): 435.20 (M+H)$^+$ (35%), 457.13 (M+Na)$^+$; UPLC Purity: 98.88%, Ret.time: 4.198 min.

Intermediate 11: 4-[3-(benzyloxy)-5-(methoxycarbonyl)phenoxy]benzoic acid

Jones reagent (~60 mL) was added dropwise to a stirring solution of Methyl 3-(benzyloxy)-5-(4-formylphenoxy)benzoate (Intermediate 12) (30 g, 82.9 mmol, 1 equiv.) in acetone (200 mL) at room temperature until a brown color persists. The reaction mixture was diluted with water and extracted several times with dichloromethane. The combined organic extracts was washed with brine, dried over anhydrous sodium sulphate, filtered and concentrated to furnish acid as white solid (30 g).

$^1$H NMR (CDCl$_3$, 400 MHz) δ ppm: 3.90 (s, 3 H), 5.1 (s, 2 H), 6.88 (t, J=2.4 Hz, 1 H), 7.02 (d, J=8.8 Hz, 2 H), 7.32-7.36 (m, 2 H), 7.37-7.43 (m, 4 H), 7.51 (s, 1 H), 8.09 (d, J=8.8 Hz, 2 H); UPLC Purity: 99.08%, Ret.time.: 4.99 min.

Intermediate 12: Methyl 3-(benzyloxy)-5-(4-formylphenoxy)benzoate

To a single necked round bottomed flask (500 mL) fitted with N$_{2(g)}$ balloon, Methyl 3-benzyloxy-5-hydroxybenzoate (Intermediate 5) (24 g, 93 mmol, 1 equiv.) followed by DMF (130 mL, 5 v/w) were added. To this stirring solution, potassium carbonate (38 g, 279 mmol, 3 equiv.) was added at room temperature. The mixture was stirred at the same temperature for 10 minutes. 4-Fluorobenzaldehyde (13.84 g, 111.62 mmol, 1.2 equiv.) was added. The reaction mixture was heated at 90° C. for 16 h. The progress of the reaction was monitored by TLC. After completion, the reaction was diluted with water and extracted with ethyl acetate. Combined organic layers were washed with brine and dried over anhydrous sodium sulphate to furnish title compound as thick yellow liquid (32.5 g). The product can be purified by column chromatography by eluting with 10% ethyl acetate:pet ether as mobile phase.

$^1$H NMR: (CDCl$_3$, 400 MHz) δ ppm: 3.90 (s, 3 H), 5.10 (s, 2 H), 6.89 (t, J=2.4 Hz, 1 H), 6.88 (t, J=2.4 Hz, 1 H), 7.07 (d, J=8.8 Hz, 2 H), 7.32-7.40 (m, 5 H), 7.53 (s, 1 H), 7.88 (d, J=8.8 Hz, 2 H), 9.94 (s, 1 H); UPLC Purity: 98.84%, Ret.time.: 5.42 min.

The following examples were prepared by using the similar procedure as in Example 2.1 with suitable variations, modifications well within the scope of a skilled person.

Example 2.2

3-(Cyclohexylmethoxy)-5-(4-(5-methyl-1,3,4-oxadiazol-2-yl)phenoxy)-N-(thiazol-2-yl)benzamide $^1$H NMR (CDCl$_3$, 400 MHz) δ ppm: 1.00-1.09 (m, 2 H), 1.18-1.34 (m, 4 H), 1.69-1.72 (m, 3 H), 1.75-1.86 (m, 2 H), 2.61 (s, 3 H), 3.78 (d, J=6 Hz, 2 H), 6.83 (s, 1 H), 7.00 (d, J=3.2 Hz, 1 H), 7.12 (d, J=8.8 Hz, 2 H), 7.18 (s, 1 H), 7.29 (s, 1 H), 7.38 (s, 1 H), 8.01 (d, J=8.4 Hz, 2 H), 10.63 (s, 1 H); UPLC Purity: 96.19%, Ret.time.: 5.77 min.

Example 2.3

3-(Cyclohexylmethoxy)-5-(4-(5-methyl-1,3,4-oxadiazol-2-yl)phenoxy)-N-(4-methyl thiazol-2-yl)benzamide $^1$H NMR (CDCl$_3$, 400 MHz) δ ppm: 1.00-1.09 (m, 2 H), 1.18-1.34 (m, 4 H), 1.69-1.72 (m, 3 H), 1.75-1.86 (m, 2 H), 2.38 (s, 3 H), 2.61 (s, 3 H), 3.78 (d, J=6 Hz, 2 H), 6.82 (d, J=2 Hz, 1 H), 6.95 (s, 1 H), 7.12 (d, J=8.8 Hz, 2 H), 7.19 (s, 1 H), 7.28 (s, 1 H), 8.02 (d, J=8.8 Hz, 2 H); UPLC Purity: 98.08%, Ret.time.: 5.96 min.

Example 2.4

3-(Allyloxy)-5-(4-(5-methyl-1,3,4-oxadiazol-2-yl)phenoxy)-N-(thiazol-2-yl)benzamide $^1$H NMR (CDCl$_3$, 400 MHz) δ ppm: 2.62 (s, 3 H), 4.67 (d, J=5.6 Hz, 2 H), 5.31 (dd, J=10.8, 1.2 Hz, 1 H), 5.43 (dd, J=10.2, 1.2 Hz, 1 H), 6.01-6.09 (m, 1 H), 6.87 (t, J=2 Hz, 1 H), 7.00 (d, J=3.6 Hz, 1 H), 7.13 (d, J=8.8 Hz, 2 H), 7.36 (t, J=1.6 Hz, 1 H), 7.40 (d, J=3.6 Hz, 1 H), 7.46 (t, J=1.6 Hz, 1 H), 8.02 (d, J=8.8 Hz, 2 H); ESI-MS: m/z (relative intensities): 435.1 (M+H)$^+$, (100%), 457 (M+Na)$^+$, (5%); UPLC Purity: 97.50%, Ret.time.: 4.49 min.

Example 2.5

3-Isobutoxy-5-(4-(5-methyl-1,3,4-oxadiazol-2-yl)phenoxy)-N-(thiazol-2-yl)benzamide $^1$H NMR (CDCl$_3$, 400 MHz) δ ppm: 1.02 (d, J=6.8 Hz, 6 H), 2.05-2.12 (m, 1 H), 2.61 (s, 3 H), 3.74 (d, J=6.4 Hz, 2 H), 6.85 (t, J=2.4 Hz, 1 H), 7.00 (d, J=3.6 Hz, 1 H), 7.13 (d, J=8.8 Hz, 2 H), 7.21 (s, 1 H), 7.29-7.32 (m, 2 H), 8.03-8.00 (d, J=8.8 Hz, 2 H), 11.3 (bs, 1 H); UPLC Purity: 97.47%, Ret.time.: 5.07 min.

Example 2.6

3-(4-(5-Methyl-1,3,4-oxadiazol-2-yl)phenoxy)-5-((tetrahydro-2H-pyran-4-yl)methoxy)-N-thiazol-2-yl)benzamide $^1$H NMR (CDCl$_3$, 400 MHz) δ ppm: 1.40-1.51 (m, 2 H), 1.73-1.76 (m, 2 H), 2.04-2.10 (m, 1 H), 2.61 (s, 3 H), 3.44 (dt, J=7.2, 2 Hz, 2 H), 3.84 (d, J=6.4 Hz, 2 H), 4.00-4.04 (m, 2 H), 6.83 (t, J=2.4 Hz, 1 H), 7.00 (d, J=1.2 Hz, 1 H), 7.14 (d, J=8.8 Hz, 2 H), 7.21 (s, 1 H), 7.30 (s, 1 H), 7.35 (s, 1 H), 8.02 (d, J=8.8 Hz, 2 H); ESI-MS m/z (relative intensities): 493.13 (M+H)+, (100%); UPLC Purity: 92%, Ret.time: 4.322 min.

Example 2.7

Ethyl 2-(2-(3-((1-methoxypropan-2-yl)oxy)-5-(4-(5-methyl-1,3,4-oxadiazol-2-yl)phenoxy)benzamido)thiazol-4-yl)acetate $^1$H NMR (CDCl$_3$, 400 MHz) δ ppm: 1.22 (t, J=7.2 Hz, 3 H), 1.32 (d, J=6.4 Hz, 3 H), 2.62 (s, 3 H), 3.40 (s, 3 H), 3.49-3.53 (m, 1 H), 3.57-3.61 (m, 1 H), 3.67 (s, 2 H), 4.18 (q, J=7.2 Hz, 2 H), 4.60-4.64 (m, 1 H), 6.84 (s, 1 H), 6.87 (t, J=2 Hz, 1 H), 7.11 (t, J=2 Hz, 1 H), 7.13 (d, J=8.8 Hz, 2 H), 7.30 (t, J=2 Hz, 1 H), 8.02 (d, J=8.8 Hz, 2 H), 9.90 (bs, 1 H); ESI-MS m/z (relative intensities): 553.1, (100%); UPLC Purity: 97.93%, Ret.time: 4.59 min.

Example 2.8

2-(2-(34(1-Methoxypropan-2-yl)oxy)-5-(4-(5-methyl-1,3,4-oxadiazol-2-yl)phenoxy)benzamido)thiazol-4-yl)acetic acid $^1$H NMR (CDCl$_3$, 400 MHz) δ ppm: 1.31 (d, J=6.4 Hz, 3 H), 2.61 (s, 3 H), 3.40 (s, 3 H), 3.47-3.50 (m, 1 H), 3.58-3.61 (m, 1 H), 3.66 (s, 2 H), 4.66-4.70 (m, 1 H), 6.75 (s, 1 H), 6.84 (s, 1 H), 7.11 (d, J=8.8 Hz, 2 H), 7.40 (s, 1 H), 7.47 (s, 1 H), 8.00 (d, J=8.4 Hz, 2 H); ESI-MS m/z (relative intensities): 525.1, (100%); UPLC Purity: 99.71%, Ret.time: 3.9 min.

Example 2.9

3-((1-Methoxypropan-2-yl)oxy)-5-(4-(5-methyl-1,3,4-oxadiazol-2-yl)phenoxy)-N-(5-methylthiazol-2-yl)benzamide $^1$H NMR: (CDCl$_3$, 400 MHz) δ ppm: 1.61 (d, J=6.4 Hz, 3 H), 2.39 (s, 3 H), 2.62 (s, 3 H), 3.39 (s, 3 H), 3.48-3.51 (m, 1 H), 3.55-3.59 (m, 1 H); 4.68-4.56 (m, 1 H), 6.86 (t, J=2 Hz, 1 H), 6.96 (s, 1 H), 7.12 (d, J=8.8 Hz, 2 H), 7.17 (s, 1 H), 7.32 (s, 1 H), 8.02 (d, J=8.8 Hz, 2 H), 10.78 (bs, 1 H); ESI-MS m/z (relative intensities): 481.13 (M+H)+ (100%); UPLC Purity: 98.99%, Ret.time.: 4.44 min.

Example 2.10

3-((1-Methoxypropan-2-yl)oxy)-5-(4-(5-methyl-1,3,4-oxadiazol-2-yl)phenoxy)-N-(4-methylthiazol-2-yl)benzamide $^1$H NMR: (CDCl$_3$, 400 MHz) δ ppm: 1.34 (d, J=6.4 Hz, 3 H), 2.32 (s, 3 H), 2.63 (s, 3 H), 3.42 (s, 3 H), 3.50-3.54 (m, 1 H), 3.57-3.61 (m, 1 H), 4.59-4.64 (m, 1 H), 6.58 (s, 1 H), 6.88 (t, J=2 Hz, 1 H), 7.12 (d, J=8.8 Hz, 2 H), 7.14-7.15 (m, 1 H), 7.30 (s, 1 H), 8.02 (d, J=8.8 Hz, 2 H); ESI-MS m/z (relative intensities): 481.12 (M+H)+ (100%); UPLC Purity: 98.33%, Ret.time: 4.44 min.

Example 2.11

(S)-3-((1-Methoxypropan-2-yl)oxy)-5-(4-(5-methyl-1,3,4-oxadiazol-2-yl)phenoxy)-N-(5-methylthiazol-2-yl)benzamide $^1$H NMR (CDCl$_3$, 400 MHz) δ ppm: 1.32 (d, J=6.4 Hz, 3 H), 2.40 (s, 3 H), 2.62 (s, 3 H), 3.40 (s, 3 H), 3.48-3.52 (m, 1 H), 3.56-3.60 (m, 1 H), 4.58-4.62 (m, 1 H), 6.86 (t, J=2 Hz, 1 H), 6.99 (s, 1 H), 7.12 (d, J=8.8 Hz, 2 H), 7.17 (s, 1 H), 7.32 (s, 1 H), 8.02 (d, J=8.8 Hz, 2 H); UPLC Purity: 99.65%, Ret.time: 4.47 min.

Example 2.12

3-(But-3-en-1-yloxy)-5-(4-(5-methyl-1,3,4-oxadiazol-2-yl)phenoxy)-N-(4-methylthiazol-2-yl)benzamide $^1$H NMR (CDCl$_3$, 400 MHz) δ ppm: 2.22 (s, 3 H), 2.55 (t, J=6.4 Hz, 2 H), 2.61 (s, 3 H), 4.03 (t, J=6.4 Hz, 2 H), 5.11 (dd, J=10.4, 1.2 Hz, 1 H), 5.15 (dd, J=17.2, 1.2 Hz, 1 H), 5.83-5.91 (m, 1 H), 6.56 (d, J=0.8 Hz, 1 H), 6.82 (t, J=2 Hz, 1 H), 7.06 (t, J=1.6 Hz, 1 H), 7.11 (d, J=8.8 Hz, 2 H), 7.23 (t, J=2 Hz, 1 H), 8.02 (d, J=8.8 Hz, 2 H), 10.2 (bs, 1 H); ESI-MS m/z (relative intensities): 463.11 (M+H)+, (30%), 485.11 (M+Na)+, (30%) UPLC Purity: 97.28%, Ret.time: 4.92 min.

Example 2.13

3-(But-3-en-1-yloxy)-5-(4-(5-methyl-1,3,4-oxadiazol-2-yl)phenoxy)-N-(5-methylthiazol-2-yl)benzamide $^1$H NMR (CDCl$_3$, 400 MHz) δ ppm: 2.38 (s, 3 H), 2.54 (t, J=6.8 Hz, 2 H), 2.62 (s, 3 H), 4.03 (t, J=6.8 Hz, 2 H), 5.11 (dd, J=10.4, 1.2 Hz, 1 H), 5.15 (dd, J=17.2, 1.2 Hz, 1 H), 5.84-5.90 (m, 1 H), 6.83 (t, J=2 Hz, 1 H), 6.91 (d, J=1.2 Hz, 1 H), 7.11 (d, J=8.8 Hz, 2 H), 7.19 (t, J=2 Hz, 1 H), 7.29 (t, J=2 Hz, 1 H), 8.02 (d, J=8.8 Hz, 2 H), 11.2 (bs, 1 H); ESI-MS m/z (relative intensities): 463.18 (M+H)+, (60%), 485.11 (M+Na)+, (100%); UPLC Purity: 99.30%, Ret.time: 4.93 min.

Example 2.14

3-(Allyloxy)-5-(4-(5-methyl-1,3,4-oxadiazol-2-yl)phenoxy)-N-(5-methylthiazol-2-yl)benzamide $^1$H NMR (CDCl$_3$, 400 MHz) δ ppm: 2.38 (s, 3 H), 2.62 (s, 3 H), 4.56 (d, J=5.2 Hz, 2 H), 5.11 (dd, J=10.4, 1.2 Hz, 1 H), 5.15 (dd, J=17.2, 1.2 Hz, 1 H), 5.98-6.07 (m, 1 H), 6.84 (t, J=2 Hz, 1 H), 6.91 (d, J=1.2 Hz, 1 H), 7.11 (d, J=8.8 Hz, 2 H), 7.20 (t, J=1.6 Hz, 1 H), 7.30 (d, J=1.6 Hz, 1 H), 8.01 (d, J=8.8 Hz, 2 H), 11.3 (bs, 1 H); ESI-MS m/z (relative intensities): 449.12 (M+H)+, (30%), 471.12 (M+Na)+, (25%); UPLC Purity: 98.06%, Ret.time: 4.67 min.

Example 2.15

(R)-3-(1-Methoxypropan-2-yloxy)-5-(4-(5-methyl-1,3,4-oxadiazol-2-yl)phenoxy)-N-(thiazol-2-yl)benzamide $^1$H NMR (DMSO-d$_6$, 400 MHz) δ ppm: 1.25 (d, J=6.4 Hz, 3 H), 2.56 (s, 3 H), 3.28 (s, 3 H), 3.46-3.58 (m, 2 H), 4.75-4.79 (m, 1 H), 6.97 (t, J=2.0 Hz, 1 H), 7.23 (d, J=8.8 Hz, 2 H), 7.29 (s, 1 H), 7.35 (s, 1 H), 7.54-7.58 (m, 2 H), 8.01 (d, J=8.8 Hz, 2 H), 12.66 (s, 1 H); UPLC Purity: 97.65%, Ret.time.: 4.24 min.

Example 2.16

Ethyl 2-{3-[(1-methoxypropan-2-yl)oxy]-5-[4-(5-methyl-1,3,4-oxadiazol-2-yl)phenoxy]benzamido}thiazole-5-carboxylate $^1$H NMR (DMSO-d$_6$, 400 MHz) δ ppm: 1.27 (t, J=7.2 Hz, 3 H), 1.31 (t, J=7.2 Hz, 3 H), 2.56 (s, 3 H), 3.28 (s, 3 H), 3.50

(t, J=6 Hz, 2 H), 4.26 (q, J=7.2 Hz, 2 H), 4.75-4.79 (m, 1 H), 7.01 (t, J=2 Hz, 1 H), 7.23 (d, J=8.8 Hz, 2 H), 7.37 (s, 1 H), 7.57 (s, 1 H), 8.01 (d, J=8.8 Hz, 2 H), 8.22 (s, 1 H), 13.13 (bs, 1 H); ESI-MS m/z (relative intensities): 539.14 (M+H)$^+$, (70%), 561.15 (M+Na)$^+$ (100%); UPLC Purity: 95.18%, Ret.time: 4.48 min.

Example 2.17

2-{3-[(1-Methoxypropan-2-yl)oxy]-5-[4-(5-methyl-1,3,4-oxadiazol-2-yl)phenoxy]benzamido}thiazole-4-carboxylic acid $^1$H NMR (DMSO-d$_6$, 400 MHz) δ ppm: 1.26 (d, J=6.4 Hz, 3 H); 2.56 (s, 3 H), 3.28 (s, 3 H), 3.46-3.51 (m, 2 H), 4.75-4.79 (m, 1 H), 6.97 (s, 1 H), 7.23 (d, J=8.8 Hz, 2 H), 7.37 (s, 1 H), 7.59 (s, 1 H), 7.98 (d, J=8.8 Hz, 2 H), 8.03 (s, 1 H), 12.98 (bs, 1 H), 13.013 (s, 1 H); ESI-MS: m/z (relative intensities): 511.08 (M+H)$^+$, (10%), 533.01 (60%) (M+Na)$^+$ UPLC Purity: 96.45%, Ret.time.: 3.93 min.

Example 2.18

2-{3-[(1-Methoxypropan-2-yl)oxy]-5-[4-(5-methyl-1,3,4-oxadiazol-2-yl)phenoxy]benzamido}thiazole-5-carboxylic acid $^1$H NMR (DMSO-d$_6$, 400 MHz) δ ppm: 1.26 (d, J=6.4 Hz, 3 H), 2.56 (s, 3 H), 3.32 (s, 3 H), 3.45-3.53 (m, 2 H), 4.76-4.80 (m, 1 H), 6.99 (s, 1 H), 7.24 (d, J=8.8 Hz, 2 H), 7.36 (m, 1 H), 7.57 (s, 1 H), 8.06 (d, J=8.8 Hz, 2 H), 8.09 (s, 1 H), 13.09 (bs, 2 H); ESI-MS m/z (relative intensities): 511.50 (M+H)$^+$ (75%), 533.57 (M+Na)$^+$ (100%); UPLC Purity: 98.26%, Ret.time.: 3.91 min.

Example 2.19

Ethyl 2-{3-[(1-methoxypropan-2-yl)oxy]-5-[4-(5-methyl-1,3,4-oxadiazol-2-yl)phenoxy]benzamido}thiazole-4-carboxylate $^1$H NMR (CDCl$_3$, 400 MHz) δ ppm: 1.26 (d, J=6.4 Hz, 3 H), 1.38 (t, J=7.2 Hz, 3 H), 2.62 (s, 3 H), 3.40 (s, 3 H), 3.50-3.53 (m, 1 H), 3.57-3.61 (m, 1 H), 4.39 (q, J=7.2 Hz, 2 H), 4.60-4.64 (m, 1 H), 6.90 (t, J=2 Hz, 1 H), 7.11-7.12 (m, 1 H), 7.14 (d, J=8.4 Hz, 2 H), 7.29 (s, 1 H), 7.87 (s, 1 H), 8.04 (d, J=8.8 Hz, 2 H), 10.00 (bs, 1 H); ESI-MS m/z (relative intensities): 539.14 (M+H)$^+$ (30%), 561.15 (M+Na)$^+$; UPLC Purity: 93.32%, Ret.time: 4.65 min.

Example 2.20

(S)-3-((1-Methoxypropan-2-yl)oxy)-5-(4-(5-methyl-1,3,4-oxadiazol-2-yl)phenoxy)-N-(4-methylthiazol-2-yl)benzamide $^1$H NMR (CDCl$_3$, 400 MHz) δ ppm: 1.31 (d, J=6.4, 3H), 2.19 (s, 3 H), 2.61 (s, 3 H), 2.39 (s, 3 H), 3.39-3.51 (m, 1 H), 3.55-3.59 (m, 1 H), 4.54-4.58 (m, 1 H), 6.56 (bs, 1 H), 6.86 (t, J=2 Hz, 1 H), 7.04 (bs, 1 H), 7.08 (d, J=8.8 Hz, 2 H), 7.27 (s, 1 H), 8.00 (d, J=8.8 Hz, 2 H), 10.05 (bs, 1 H); UPLC Purity: 99.27%, Ret.time: 4.45 min.

Example 2.21

3-((1-Methoxypropan-2-yl)oxy)-5-(3-(5-methyl-1,3,4-oxadiazol-2-yl)phenoxy)-N-(thiazole-2-yl)benzamide $^1$H NMR (CDCl$_3$, 400 MHz) δ ppm: 1.31 (d, J=6.4 Hz, 3 H), 2.61 (s, 3 H), 3.39 (s, 3 H), 3.47-3.51 (m, 1 H), 3.54-3.59 (m, 1 H), 4.55-4.62 (m, 1 H), 6.88 (s, 1 H), 6.98 (d, J=3.6 Hz 1 H), 7.17 (m, 1 H), 7.19 (s, 1 H), 7.25 (s, 1 H), 7.32 (s, 1 H), 7.48 (t, J=7.4 Hz, 1 H), 7.68 (s, 1 H), 7.81 (d, J=7.6 Hz, 1 H), 11.63 (s, 1 H); ESI-MS m/z (relative intensities): 467.36 (M+H)$^+$ (100%), 466.46 (M+Na)$^+$ (100%); UPLC Purity: 99.06%, Ret.time.: 4.29 min.

Example 2.22

3-(4-(5-Isobutyl-1,3,4-oxadiazol-2-yl)phenoxy)-5-((1-methoxypropan-2-yl)oxy)-N-(thiazol-2-yl)benzamide $^1$H NMR (400 MHz, CDCl$_3$) δ ppm: 1.06 (d, J=6.4 Hz, 6 H), 1.33 (d, J=6 Hz, 3 H), 2.2-2.28 (m, 1 H), 2.81 (d, J=7.2 Hz, 2 H), 3.40 (s, 3 H), 3.48-3.52 (m, 1 H), 3.56-3.60 (m, 1 H), 4.58-4.62 (m, 1 H), 6.88 (t, J=2 Hz, 1 H), 7.00 (d, J=3.6 Hz, 1 H), 7.13 (d, J=8.8 Hz, 2 H), 7.17 (bs, 1 H), 7.33-7.36 (m, 2 H), 8.03 (d, J=8.8 Hz, 2 H), 10.64 (bs, 1 H); ESI-MS m/z (Relative intensities): 509.0 (M+H)$^+$ (100%); UPLC Purity: 98.34%, Ret.time: 5.08 min.

Example 2.23

3-(4-(5-Isobutyl-1,3,4-oxadiazol-2-yl)phenoxy)-5-((1-methoxypropan-2-yl)oxy)-N-(4-methylthiazol-2-yl)benzamide $^1$H NMR (400 MHz, CDCl$_3$): δ ppm 1.06 (d, J=6.4 Hz, 6 H), 1.32 (d, J=6.4 Hz, 3 H), 2.22-2.25 (m, 1 H), 2.26 (s, 3 H), 2.81 (d, J=7.2 Hz, 2 H), 3.39 (s, 3 H), 3.48-3.52 (m, 1 H), 3.55-3.59 (m, 1 H), 4.55-4.59 (m, 1 H), 6.56 (t, J=1.2 Hz, 1 H), 6.86 (t, J=2 Hz, 1 H), 7.09 (d, J=8.8 HZ, 2 H), 7.10 (s, 1 H), 7.29 (s, 1 H), 8.01 (d, J=8.8 Hz, 2 H), 10.1 (bs, 1 H); ESI-MS m/z (Relative intensities): 523.0 (M+H)$^+$ (100%); UPLC Purity: 98.77%, Ret.time.: 5.27 min.

Example 2.24

3-(4-(5-Isobutyl-1,3,4-oxadiazol-2-yl)phenoxy)-5-((1-methoxypropan-2-yl)oxy)-N-(5-methylthiazol-2-yl)benzamide $^1$H NMR (400 MHz, CDCl$_3$): δ ppm 1.06 (d, J=6.4 Hz, 6 H), 1.31 (d, J=6.4 Hz, 3 H), 2.20-2.27 (m, 1 H), 2.37 (s, 3 H), 2.81 (d, J=7.2 Hz, 2 H), 3.39 (s, 3 H), 3.47-3.51 (m, 1 H), 3.55-3.59 (m, 1 H), 4.56-4.60 (m, 1 H), 6.86 (t, J=2 Hz, 1 H), 6.89 (s, 1 H), 7.11 (d, J=8.8 Hz, 2 H), 7.19 (t, J=1.6 Hz, 1 H), 7.33 (t, J=7.33 Hz, 1 H), 8.01 (d, J=8.8 Hz, 2 H); ESI-MS m/z (Relative intensities): 523.1 (M+H)$^+$ (100%); UPLC Purity: 98.13%, Ret.time.: 5.28 min.

Example 2.25

3-(4-(5-Ethyl-1,3,4-oxadiazol-2-yl)phenoxy)-5-((1-methoxypropan-2-yl)oxy)-N-(thiazol-2-yl)benzamide $^1$H NMR (400 MHz, CDCl$_3$): δ ppm 1.32 (d, J=6.4 Hz, 3 H), 1.44 (t, J=7.6 Hz, 3 H), 2.94 (q, J=7.6 Hz, 2 H), 3.39 (s, 3

H), 3.48-3.51 (m, 1 H), 3.55-3.59 (m, 1 H), 4.55-4.61 (m, 1 H), 6.87 (t, J=2.4 Hz, 1 H), 6.98 (d, J=3.2 Hz, 1 H), 7.11 (d, J=8.8 Hz, 2 H), 7.19 (t, J=1.6 Hz, 1 H), 7.28 (d, J=3.2 Hz, 1 H), 7.34 (t, J=1.6 Hz, 1 H), 8.01 (d, J=8.8 Hz, 2 H), 10.4 (bs, 1 H); ESI-MS m/z (Relative intensities): 481.0 (M+H)⁺ (100%); UPLC Purity: 95.64%, Ret.time: 4.49 min.

Example 2.26

3-(4-(5-Ethyl-1,3,4-oxadiazol-2-yl)phenoxy)-5-((1-methoxypropan-2-yl)oxy)-N-(4-methylthiazol-2-yl)benzamide ¹H NMR (400 MHz, CDCl₃): δ ppm 1.31 (d, J=6.4 Hz, 3 H), 1.44 (t, J=7.6 Hz, 3 H), 2.21 (s, 3 H), 2.95 (q, J=7.6 Hz, 2 H), 3.39 (s, 3 H), 3.47-3.51 (m, 1 H), 3.55-3.59 (m, 1 H), 4.54-4.59 (m, 1 H), 6.56 (s, 1 H), 6.85 (t, J=2 Hz, 1 H), 7.07 (t, J=1.6 Hz, 1 H), 7.09 (d, J=8.4 Hz, 2 H), 7.27 (t, J=1.6 Hz, 1 H), 8.02 (d, J=8.8 Hz, 2 H); ESI-MS m/z (Relative intensities): 494.9 (M+H)⁺ (100%); UPLC Purity: 93.78%, Ret.time.: 4.70 min.

Example 2.27

3-(4-(5-Ethyl-1,3,4-oxadiazol-2-yl)phenoxy)-5-((1-methoxypropan-2-yl)oxy)-N-(5-methylthiazol-2-yl)benzamide ¹H NMR (400 MHz, CDCl₃): δ ppm 1.32 (d, J=6.4 Hz, 3 H), 1.44 (t, J=7.6 Hz, 3 H), 2.39 (s, 3 H), 2.96 (q, J=7.6 Hz, 2 H), 3.39 (s, 3 H), 3.48-3.52 (m, 1 H), 3.55-3.59 (m, 1 H), 4.57-4.61 (m, 1 H), 6.87 (t, J=2 Hz, 1 H), 6.94 (s, 1 H), 7.11 (d, J=8.8 Hz, 2 H), 7.17 (t, J=1.6 Hz, 1 H), 7.32 (t, J=1.6 Hz, 1 H), 8.01 (d, J=8.8 Hz, 2 H): ESI-MS m/z (relative intensities): 494.9 (M+H)⁺ (100%); UPLC Purity: 93.78%, Ret.time.: 4.70 min.

Example 2.28

3-(4-(5-Cyclopropyl-1,3,4-oxadiazol-2-yl)phenoxy)-5-((1-methoxypropan-2-yl)oxy)-N-(thiazol-2-yl)benzamide ¹H NMR (400 MHz, CDCl₃): δ ppm 1.16-1.28 (m, 4 H), 1.32 (d, J=6.4 Hz, 3 H), 2.19-2.26 (m, 1 H), 3.39 (s, 3 H), 3.48-3.50 (m, 1 H), 3.55-3.59 (m, 1 H), 4.57-4.61 (m, 1 H), 6.87 (t, J=2 Hz, 1 H), 6.98 (d, J=3.6 Hz, 1 H), 7.01 (d, J=8.8 Hz, 2 H), 7.19 (s, 1 H), 7.27 (s, 1 H), 7.34 (s, 1 H), 7.98 (d, J=8.8 Hz, 2 H); ESI-MS m/z (Relative intensities): 493 (M+H)⁺'' (100%); UPLC Purity: 98.2%, Ret.time: 4.56 min.

Example 2.29

3-(4-(5-Cyclopropyl-1,3,4-oxadiazol-2-yl)phenoxy)-5-((1-methoxypropan-2-yl)oxy)-N-(4-methylthiazol-2-yl)benzamide ¹H NMR (400 MHz, CDCl₃): δ ppm 1.20-1.25 (m, 4 H), 1.31 (d, J=6.4 Hz, 3 H), 2.17 (s, 3 H), 2.19-2.25 (m, 1 H), 3.39 (s, 3 H), 3.47-3.51 (m, 1 H), 3.54-3.58 (m, 1 H), 4.52-4.56 (m, 1 H), 6.56 (d, J=1.2 Hz, 1 H), 6.85 (t, J=2 Hz, 1 H), 7.03-7.04 (m, 1 H), 7.07 (d, J=8.8 Hz, 2 H), 7.27 (s, 1 H), 7.99 (d, J=8.8 Hz, 2 H), 10.6 (bs, 1 H); ESI-MS m/z (Relative intensities): 507 (M+H)⁺ (100%); UPLC Purity: 97.64%, Ret.time: 4.76 min.

Example 2.30

3-(4-(5-Cyclopropyl-1,3,4-oxadiazol-2-yl)phenoxy)-54(1-methoxypropan-2-yl)oxy)-N-(5-methylthiazol-2-yl)benzamide ¹H NMR (400 MHz, CDCl₃): δ ppm 1.28-1.29 (m, 4 H), 1.31 (d, J=6.4 Hz, 3 H), 2.19-2.26 (m, 1 H), 2.37 (s, 3 H), 3.39 (s, 3 H), 3.47-3.51 (m, 1 H), 3.54-3.59 (m; 1 H), 4.54-4.59 (m, 1 H), 6.85 (d, J=2 Hz, 1 H), 6.88 (s, 1 H), 7.09 (d, J=8.8 Hz, 2 H), 7.18 (s, 1 H), 7.32 (s, 1 H), 7.97 (d, J=8.8 Hz, 2 H), 11.50 (bs, 1 H); ESI MS m/z (Relative intensities): 507 (M+H)⁺ (100%); UPLC Purity: 97.85%, Ret.time: 4.76 min.

Example 2.31

3-(4-(5-Cyclopentyl-1,3,4-oxadiazol-2-yl)phenoxy)-54(1-methoxypropan-2-yl)oxy)-N-(thiazol-2-yl)benzamide ¹H NMR (400 MHz, CDCl₃): δ ppm 1.33 (d, J=6.4 Hz, 3 H), 1.84-1.88 (m, 2 H), 1.96-1.98 (m, 2 H), 1.99-2.13 (m, 2 H), 2.15-2.17 (m, 2 H), 3.36-3.40 (m, 1 H), 3.39 (s, 3 H), 3.47-3.51 (m, 1 H), 3.54-3.59 (m, 1 H), 4.58-4.59 (m, 1 H), 6.87 (t, J=2 Hz, 1 H), 6.96 (d, J=3.6 Hz, 1 H), 7.11 (d, J=8.8 Hz, 2 H), 7.20-7.21 (m, 2 H), 7.35 (t, J=2 Hz, 1 H), 8.01 (d, J=8.8 Hz, 2 H), 12.0 (bs, 1 H); ESI MS m/z (Relative intensities): 521 (M+H)⁺ (100%), 442.6 (M+Na) (15%) (+ve mode); UPLC Purity: 98.20%, Ret.time.: 5.13 min.

Example 2.32

3-(4-(5-Cyclopentyl-1,3,4-oxadiazol-2-yl)phenoxy)-5-((1-methoxypropan-2-yl)oxy)-N-(4-methylthiazol-2-yl)benzamide ¹H NMR (400 MHz, CDCl₃): δ ppm 1.32 (d, J=6.4 Hz, 3 H), 1.72-1.75 (m, 2 H), 1.84-1.87 (m, 2 H), 1.99-2.02 (m, 2 H), 2.14-2.26 (m, 2 H), 2.26 (s, 3 H), 3.38-3.41 (m, 1 H), 3.40 (s, 3 H), 3.48-3.51 (m, 1 H), 3.55-3.59 (m, 1 H), 4.55-4.59 (m, 1 H), 6.56 (s, 1 H), 6.86 (t, J=2 Hz, 1 H), 7.08-7.09 (m, 1 H), 7.11 (d, J=8.8 Hz, 2 H), 7.27 (t, J=2 Hz, 1 H), 8.02 (d, J=8.8 Hz, 2 H), 10 (bs, 1 H); ESI MS m/z (relative intensities): 534.9 (M+H)⁺ (100%), 557 (M+Na)⁺ (30%); UPLC Purity: 98.17%, Ret.time.: 5.32 min.

Example 2.33

3-(Cyclohexylmethoxy)-5-(4-(5-methyl-1,3,4-oxadiazol-2-yl)phenoxy)-N-(5-methyl thiazol-2-yl)benzamide ¹H NMR (DMSO-d₆, 400 MHz) δ ppm: 1.14-1.30 (m, 5 H), 1.63-1.82 (m, 6 H), 2.35 (s, 3 H), 2.56 (s, 3 H), 3.87 (d, J=6.0 Hz, 2 H), 6.93 (s, 1 H), 7.23-7.20 (m, 3 H), 7.35 (s, 1 H), 7.53 (s, 1 H), 8.01 (d, J=8.8 Hz, 2 H), 12.48 (bs, 1 H); ESI MS m/z (relative intensities): 505.2 (M+H)⁺, 100%; UPLC Purity: 95.79%, Ret.time: 5.892 min.

Example 2.34

3-(4-(5-Methyl-1,3,4-oxadiazol-2-yl)phenoxy)-N-(5-methylthiazol-2-yl)-5-((tetrahydro-2H-pyran-4-yl)methoxy)benzamide ¹H NMR (DMSO-d₆, 400 MHz) δ ppm: 1.31-1.35 (m, 2 H), 1.67-1.70 (m, 2 H), 1.95-2.07 (m, 1 H), 2.35 (s, 3 H), 2.56

(s, 3 H), 3.29-3.32 (m, 2 H), 3.85-3.89 (m, 2 H), 3.93 (d, J=6.4 Hz, 2 H), 6.95 (s, 1 H), 7.19 (s, 1 H), 7.20 (d, J=8.8. Hz, 2 H), 7.35 (s, 1 H), 7.55 (s, 1 H), 8.01 (d, J=8.8 Hz, 2 H), 12.48 (bs, 1 H); ESI MS m/z (relative intensities): 506.9 (M+H)$^+$ (90%); UPLC Purity: 94.87%, Ret.time: 4.51 min.

Example 2.35

3-(4-(5-Methyl-1,3,4-oxadiazol-2-yl)phenoxy)-N-(4-methylthiazol-2-yl)-5-((tetrahydro-2H-pyran-4-yl)methoxy)benzamide $^1$H NMR (DMSO-d$_6$, 400 MHz) δ ppm: 1.31-1.35 (m, 2 H), 1.67-1.70 (m, 2 H), 1.91-2.10 (m, 1 H), 2.28 (s, 3 H), 2.56 (s, 3 H), 3.31-3.33 (m, 2 H), 3.85-3.89 (m, 2 H), 3.94 (d, J=6.4 Hz, 2 H), 6.81 (s, 1 H), 6.96 (s, 1 H), 7.21 (d, J=8.8 Hz, 2 H), 7.36 (s, 1 H), 7.56 (s, 1 H), 8.01 (d, J=8.8 Hz, 2 H), 12.60 (bs, 1 H); ESI MS m/z (relative intensities): 507 (M+H)$^+$, (40%); UPLC Purity: 95.56%, Ret.time: 4.515 min.

Example 2.36

N-(5-Bromothiazol-2-yl)-3-((1-methoxypropan-2-yl)oxy)-5-(4-(5-methyl-1,3,4-oxadiazol-2-yl)phenoxy)benzamide $^1$H NMR (400 MHz, DMSO-d$_6$) δ ppm: 1.22 (d, J=6 Hz, 3 H), 2.56 (s, 3 H), 3.28 (s, 3 H), 3.45-3.53 (m, 2 H), 4.75-4.79 (m, 1 H), 6.98 (t, J=2.4 Hz, 1 H), 7.23 (d, J=8.8 Hz, 2 H), 7.34 (t, J=1.6 Hz, 1 H), 7.55 (t, J=2 Hz, 1 H), 7.65 (s, 1 H), 8.01 (d, J=8.8 Hz, 2 H), 12.93 (bs, 1 H); ESI MS m/z (relative intensities): 545 (M)$^+$ (100%), 547 (M+2)$^+$ (100%); UPLC Purity: 98.3%, Ret.time: 4.97 min.

Example 2.37

3-(1-Cyclopropylethoxy)-5-(4-(5-methyl-1,3,4-oxadiazol-2-yl)phenoxy)-N-(5-methyl thiazol-2-yl)benzamide $^1$H NMR (400 MHz, DMSO-d$_6$) δ ppm: 0.34-0.35 (m, 2 H), 0.48-0.51 (m, 2 H), 1.07-1.12 (m, 1 H), 1.28 (d, J=6.4 Hz, 3 H), 2.35 (s, 3 H), 2.56 (s, 3 H), 4.10-4.12 (m, 1 H), 6.92 (t, J=2.0 Hz, 1 H), 7.19 (s, 1 H), 7.21 (d, J=8.8 Hz, 2 H), 7.32 (t, J=2.0 Hz, 1 H), 7.49 (t, J=2.0 Hz, 1 H), 8.00 (d, J=8.8 Hz, 2 H), 12.56 (bs, 1 H); ESI MS m/z (relative intensities): 476.9 (M+H)$^+$ (100%); UPLC Purity: 92.9%, Ret.time: 5.016 min.

Example 2.38

3-(1-Cyclopropylethoxy)-5-(4-(5-methyl-1,3,4-oxadiazol-2-yl)phenoxy)-N-(4-methyl thiazol-2-yl)benzamide $^1$H NMR (400 MHz, DMSO-d$_6$) δ ppm: 0.23-0.41 (m, 2 H), 0.47-0.57 (m, 2 H), 1.08-1.14 (m, 1 H), 1.31 (d, J=6.4 Hz, 3 H), 2.28 (s, 3 H), 2.56 (s, 3 H), 4.12-4.09 (m, 1 H), 6.81 (s, 1 H), 6.92 (t, J=2.0 Hz, 1 H), 7.21 (d, J=8.8 Hz, 2 H), 7.32 (t, J=2.0 Hz, 1 H), 7.50 (t, J=2.0 Hz, 1 H), 7.97-8.01 (m, 2 H), 12.57 (bs, 1 H); ESI MS m/z (relative intensities): 476.9 (M+H)$^+$ (100%); UPLC Purity: 89.52%, Ret.time: 5.006 min.

Example 2.39

3-(Cyclopropyl methoxy)-5-(4-(5-methyl-1,3,4-oxadiazol-2-yl)phenoxy)-N-(5-methyl thiazol-2-yl)benzamide $^1$H NMR (400 MHz, DMSO-d$_6$) δ ppm: 0.31-0.35 (m, 2 H), 0.55-0.60 (m, 2 H), 1.22-1.24 (m, 1 H), 2.35 (s, 3 H), 2.56 (s, 3 H), 3.92 (d, J=6.8 Hz, 2 H), 6.94 (s, 1 H), 7.20 (d, J=8.8 Hz, 2 H), 7.22 (s, 1 H), 7.35 (s, 1 H), 7.52 (s, 1 H), 7.98 (d, J=8.8 Hz, 2 H), 12.48 (s, 1 H); ESI MS m/z (relative intensities): 463 (M+H)$^+$ (100%); UPLC Purity: 94.02%, Ret.time: 4.806 min.

Example 2.40

3-(Cyclopropylmethoxy)-5-(4-(5-methyl-1,3,4-oxadiazol-2-yl)phenoxy)-N-(4-methyl thiazol-2-yl)benzamide $^1$H NMR (400 MHz, DMSO-d$_6$) δ ppm: 0.33-0.34 (m, 2 H), 0.57-0.59 (m, 2 H), 1.22-1.24 (m, 1 H), 2.28 (s, 3 H), 2.56 (s, 3 H), 4.08 (d, J=6.8 Hz, 2 H), 6.81 (s, 1 H), 6.95 (s, 1 H), 7.22 (d, J=8.4 Hz, 2 H), 7.35 (s, 1 H), 7.53 (s, 1 H), 7.99 (d, J=8.8 Hz, 2 H), 12.60 (bs, 1 H); ESI MS m/z (relative intensities): 462.9 (M+H)$^+$ (100%); UPLC Purity: 96.12%, Ret.time: 4.806 min.

Example 2.41

3-(3-Methoxybutoxy)-5-(4-(5-methyl-1,3,4-oxadiazol-2-yl)phenoxy)-N-(4-methylthiazol-2-yl)benzamide $^1$H NMR (400 MHz, DMSO-d$_6$) δ ppm: 1.13 (d, J=6.4 Hz, 3 H), 1.83-1.89 (m, 2 H), 2.28 (s, 3 H), 2.56 (s, 3 H), 3.22 (s, 3 H), 3.47-3.52 (m, 1 H), 4.10-4.14 (m, 2 H), 6.81 (s, 1 H), 6.95 (t, J=2.0 Hz, 2 H), 7.22 (d, J=8.8 Hz, 2 H), 7.55 (t, J=2.0 Hz, 1 H), 8.01 (d, J=8.8 Hz, 2 H); ESI MS m/z (relative intensities): 495.0 (M+H)$^+$ (100%); UPLC Purity: 99.1%, Ret.time: 4.673 min.

Example 2.42

(S)—N-(5-Cyanothiazol-2-yl)-3-((1-methoxypropan-2-yl)oxy)-5-(4-(5-methyl-1,3,4-oxadiazol-2-yl)phenoxy)benzamide $^1$H NMR (400 MHz, DMSO-d$_6$) δ ppm: 1.34 (d, J=6.4 Hz, 3 H), 2.62 (s, 3 H), 3.40 (s, 3 H), 3.50-3.54 (m, 1 H), 3.58-3.62 (m, 1 H), 4.60-4.64 (m, 1 H), 6.92 (t, J=2 Hz, 1 H), 7.12 (d, J=8.8 Hz, 2 H), 7.21 (t, J=2 Hz, 1 H), 7.34 (t, J=2 Hz, 1 H), 7.88 (s, 1H), 8.01 (d, J=8.8 Hz, 2 H), 11.22 (bs, 1 H); UPLC Purity: 99.31%, Ret.time: 4.52 min.

Example 2.43

Ethyl-5-chloro-2-(3-((1-methoxypropan-2-yl)oxy)-5-(4-(5-methyl-1,3,4-oxadiazol-2-yl)phenoxy)benzamido)thiazole-4-carboxylate $^1$H NMR (400 MHz, CDCl$_3$) δ ppm: 1.26 (d, J=6.4 Hz, 3 H), 1.38 (t, J=7.2 Hz, 3 H), 2.62 (s, 3 H), 3.40 (s, 3 H), 3.50-3.53 (m, 1 H), 3.56-3.61 (m, 1 H), 4.41 (q, J=7.2 Hz, 2 H), 4.59-4.63 (m, 1 H), 6.89 (t, J=2 HZ, 1 H), 7.08 (s, 1 H), 7.10 (s, 1 H), 7.13 (d, J=7.2 Hz, 2 H), 8.03 (d, J=8.8 Hz, 2 H), 9.64 (bs, 1 H), ESI MS m/z Relative intensities: 572.8 (M+1)$^+$ (100%), 594.85 (M+Na)$^+$ UPLC Purity: 88.11%, Ret.time: 5.22 min.

Example 2.44

3-((1-Methoxypropan-2-yl)oxy)-5-(4-(5-methyl-1,3,4-oxadiazol-2-yl)phenoxy)-N-(4-(2-(3-oxomorpholino)ethyl)thiazol-2-yl)benzamide $^1$H NMR (400 MHz, DMSO-d$_6$) δ ppm: 1.26 (d, J=6.4 Hz, 3 H), 2.62 (s, 3 H), 2.94 (t, J=7.2 Hz, 2 H), 3.23 (t, J=5.2 Hz, 2 H), 3.25 (s, 3 H), 3.48-3.51 (m, 1 H), 3.56-3.61 (m, 1 H), 3.71 (t, J=7.2 Hz, 2 H), 3.78-3.80 (m, 2 H), 4.14 (s, 2 H), 4.60-4.64 (m, 1 H), 6.70 (s, 1 H), 6.87 (t, J=2.4 Hz, 1 H), 7.13 (d, J=8.8 Hz, 2 H), 7.15-7.16 (m, 1 H), 7.33 (s, 1 H), 8.02 (d, J=8.8 Hz, 2 H), 9.70 (bs, 1 H), ESI MS m/z (relative intensities): 594.0 (M+H)$^+$ (75%), 615.6 (M+Na)$^+$; UPLC Purity: 96.54%, Ret.time: 3.903 min.

Example 2.45

(S)-3-((1-Methoxypropan-2-yl)oxy)-5-(4-(5-methyl-1,3,4-oxadiazol-2-yl)phenoxy)-N-(4-(2-(3-oxomorpholino)ethyl)thiazol-2-yl)benzamide $^1$H NMR (400 MHz, CDCl$_3$) δ ppm: 1.28 (d, J=6.4 Hz, 3 H), 2.62 (s, 3 H), 2.95 (t, J=7.2 Hz, 2 H), 3.24 (t, J=5.6 Hz, 2 H), 3.40 (s, 3 H), 3.48-3.51 (m, 1 H), 3.57-3.61 (m, 1 H), 3.71 (t, J=72 Hz, 2 H), 3.78-3.80 (m, 2 H), 4.14 (s, 2 H), 4.61-4.65 (m, 1 H), 6.70 (s, 1 H) 6.87 (t, J=2.4 Hz, 1 H), 7.13 (d, J=8.8 Hz, 2 H), 7.18 (s, 1 H), 7.32 (s, 1 H), 8.02 (d, J=8.8 Hz, 2 H); ESI-MS m/z (relative intensities): 594.0 (M+H)$^+$ (100%), 616.0 (M+Na)$^+$ (10%); UPLC Purity: 97.80%, Ret.time: 3.945 min.

Example 2.46

N-(4-(Hydroxymethyl)thiazol-2-yl)-3-((1-methoxypropan-2-yl)oxy)-5-(4-(5-methyl-1,3,4-oxadiazol-2-yl)phenoxy)benzamide $^1$H NMR (400 MHz, DMSO-d$_6$) δ ppm: 1.28 (d, J=6.4 Hz, 3 H), 2.56 (s, 3 H), 3.28 (s, 3 H), 3.46-3.51 (m, 2 H), 4.49 (d, J=4.8 Hz, 2 H), 4.77-4.78 (m, 1 H), 5.21 (t, J=5.6 Hz, 1 H), 6.95 (t, J=2 Hz, 1 H), 6.98 (s, 1 H), 7.24 (d, J=8.8 Hz, 2 H), 7.35 (s, 1 H), 7.56 (t, J=2 Hz, 1 H), 7.99 (d, J=8.8 Hz, 2 H), 12.63 (bs, 1 H); ESI MS m/z (relative intensities): 497.0 (M+H)$^+$ (100%); UPLC Purity: 97.20%, Ret.time: 3.74 min.

Example 2.47

3-(4-(5-(Chloromethyl)-1,3,4-oxadiazol-2-yl)phenoxy)-5-((1-methoxypropan-2-yl)oxy)-N-(thiazol-2-yl)benzamide $^1$H NMR (400 MHz, CDCl$_3$) δ ppm: 1.31 (d, J=6.4 Hz, 3 H), 3.28 (s, 3 H), 3.45-3.53 (m, 2 H), 4.76-4.80 (m, 1 H), 5.12 (s, 2 H), 6.98 (t, J=2 Hz, 1 H), 7.21 (d, J=8.8 Hz, 2 H), 7.25-7.28 (m, 1 H), 7.37 (t, J=2 Hz, 1 H), 7.55 (d, J=3.6 Hz, 1 H), 7.57 (t, J=2 Hz, 1 H), 8.01 (d, J=8.8 Hz, 2 H), 12.66 (bs, 1 H); ESI MS m/z (relative intensities): 500.9 M$^+$ (100%), 503.5 (M+2)$^+$ (100%); UPLC Purity: 94.86%, Ret.time: 4.61 min.

Example 2.48

3-((1-Methoxypropan-2-yl)oxy)-5-(4-(5-phenyl-1,3,4-oxadiazol-2-yl)phenoxy)-N-(thiazol-2-yl)benzamide $^1$H NMR (400 MHz, CDCl$_3$) δ ppm: 1.32 (d, J=6 Hz, 3 H), 3.39 (s, 3 H), 3.48-3.52 (m, 1 H), 3.55-3.59 (m, 1 H), 4.55-4.61 (m, 1 H), 6.89 (t, J=2 Hz, 1 H), 6.99 (d, J=3.6 Hz, 1 H), 7.15 (d, J=8.8 Hz, 2 H), 7.20 (t, J=2 Hz, 1 H), 7.29 (d, J=3.6 Hz, 1 H), 7.34-7.35 (m, 1 H), 7.52-7.57 (m, 3 H), 8.12-8.15 (m, 4 H), 11.22 (bs, 1 H); ESI MS m/z (relative intensities): 529.0 (M+H)$^+$ (100%); UPLC Purity: 99.41%, Ret.time: 5.15 min.

Example 2.49

3-(4-(5-Cyclohexyl-1,3,4-oxadiazol-2-yl)phenoxy)-5-((1-methoxypropan-2-yl)oxy)-N-(thiazol-2-yl)benzamide $^1$H NMR (400 MHz, CDCl$_3$) δ ppm: 1.32 (d, J=6 Hz, 3 H), 1.31-1.33 (m, 3 H), 1.63-1.73 (m, 3 H), 1.86-1.90 (m, 2 H), 2.12-2.16 (m, 2 H), 2.95-3.02 (m, 1 H), 3.39 (s, 3 H), 3.48-3.51 (m, 1 H), 3.55-3.59 (m, 1 H), 4.57-4.62 (m, 1 H), 6.87 (t, J=2 Hz, 1 H), 6.98 (d, J=3.6 Hz, 1 H), 7.12 (d, J=8.8 Hz, 2 H), 7.19 (d, J=1.6 Hz, 1 H), 7.27 (d, J=4 Hz, 1 H), 7.34 (s, 1 H), 8.02 (d, J=8.8 Hz, 2 H), 11.35 (bs, 1 H); ESI MS m/z (relative intensities): 535.1 (M+H)$^+$ (100%); UPLC Purity: 97.51%, Ret.time: 5.42 min.

Example 2.50

N-(5-Cyanothiazol-2-yl)-3-(1-methoxypropan-2-yl)oxy)-5-(4-(5-methyl-1,3,4-oxadiazol-2-yl)phenoxy)benzamide $^1$H NMR (400 MHz, CDCl$_3$) δ ppm: 1.34 (d, J=6.4 Hz, 3 H), 2.62 (s, 3 H), 3.40 (s, 3 H), 3.50-3.54 (m, 1 H), 3.58-3.62 (m, 1 H), 4.58-4.64 (m, 1 H), 6.91 (t, J=2 Hz, 1 H), 7.12 (d, J=8.8 Hz, 2 H), 7.20 (t, J=1.6 Hz, 1 H), 7.33 (t, J=2 Hz, 1 H), 7.89 (s, 1 H), 8.01 (d, J=8.8 Hz, 2 H), 11.18 (bs, 1 H); UPLC Purity: 98.91%, Ret.time: 4.52 min.

Example 2.51

3-(4-(5-Cyclopentyl-1,3,4-oxadiazol-2-yl)phenoxy)-5-((1-methoxypropan-2-yl)oxy)-N-(5-methylthiazol-2-yl)benzamide $^1$H NMR (400 MHz, CDCl$_3$) δ ppm: 1.31 (d, J=6.4 Hz, 3 H), 1.74-1.76 (m, 2 H), 1.84-1.88 (m, 2 H), 1.97-2.02 (m, 2 H), 2.12-2.18 (m, 2 H), 2.37 (s, 3 H), 3.37-3.41 (m, 4 H), 3.47-3.51 (m, 1 H), 3.55-3.59 (m, 1 H), 4.56-4.60 (m, 1 H), 6.86 (t, J=2 Hz, 1 H), 6.90 (s, 1 H), 7.11 (d, J=8.8 Hz, 2 H), 7.18 (t, J=1.6 Hz, 1 H), 7.32 (t, J=2 Hz, 1 H), 8.02 (d, J=8.8 Hz, 2 H), 11.35 (bs, 1 H); ESI MS m/z (relative intensities): 535.0 (M+H)$^+$ (100%); UPLC Purity: 97.41%, Ret.time: 5.33 min.

Example 2.52

3-((1-Methoxypropan-2-yl)oxy)-N-(5-methylthiazol-2-yl)-5-(4-(5-phenyl-1,3,4-oxadiazol-2-yl)phenoxy)benzamide $^1$H NMR (400 MHz, CDCl$_3$) δ ppm: 1.28 (d, J=6.4 Hz, 3 H), 2.11 (s, 3 H), 3.38 (s, 3 H), 3.45-3.48 (m, 1 H), 3.52-3.56 (m, 1 H), 4.47-4.53 (m, 1 H), 6.55 (s, 1 H), 6.85 (t, J=2 Hz, 1 H), 6.98 (t, J=2 Hz, 1 H), 7.08 (d, J=9.2 Hz, 2 H), 7.23 (t, J=2 Hz, 1 H), 7.52-7.56 (m, 3 H), 8.09-8.16 (m, 4 H), 10.79 (bs, 1 H); ESI MS m/z (relative intensities): 543.0 (M+H)$^+$ (100%); UPLC Purity: 99.46%, Ret.time: 5.34 min.

Example 2.53

3-((1-Methoxypropan-2-yl)oxy)-N-(4-methylthiazol-2-yl)-5-(4-(5-phenyl-1,3,4-oxadiazol-2-yl)phenoxy)benzamide $^1$H NMR (400 MHz, CDCl$_3$) δ ppm: 1.32 (d, J=6.4 Hz, 3 H), 2.38 (s, 3 H), 3.39 (s, 3 H), 3.47-3.51 (m, 1 H), 3.55-3.59

(m, 1 H), 4.56-4.60 (m, 1 H), 6.55 (s, 1 H), 6.88 (t, J=2 Hz, 1 H), 7.13 (d, J=8.8 Hz, 2 H), 7.20 (t, J=2 Hz, 1 H), 7.33 (t, J=1.6 Hz, 1 H), 7.51-7.58 (m, 3 H), 8.11 (d, J=8.8 Hz, 2 H), 8.11-8.15 (m, 2 H), 11.3 (bs, 1 H); ESI MS m/z (relative intensities): 542.9 (M+H)$^+$ (100%); UPLC Purity: 99.41%, Ret.time: 5.15 min.

Example 2.54

3-(4-(5-Cyclohexyl-1,3,4-oxadiazol-2-yl)phenoxy)-5-((1-methoxypropan-2-yl)oxy)-N-(4-methylthiazol-2-yl)benzamide $^1$H NMR (400 MHz, CDCl$_3$) δ ppm: 1.31 (d, J=6 Hz, 3 H), 1.35-1.45 (m, 3 H), 1.66-1.73 (m, 3 H), 1.85-1.89 (m, 2 H), 2.12-2.15 (m, 2 H), 2.19 (s, 3 H), 2.94-3.01 (m, 1 H), 3.39 (s, 3 H), 3.47-3.50 (m, 1 H), 3.54-3.58 (m, 1 H), 4.51-4.58 (m, 1 H), 6.56 (s, 1 H), 6.85 (t, J=2 Hz, 1 H), 7.03 (d, J=8.8 Hz, 2 H), 7.07-7.09 (m, 1 H), 7.26 (s, 1 H), 8.01 (d, J=8.4 Hz, 2 H), 10.6 (bs, 1 H); ESI MS m/z (relative intensities): 549 (M+H)$^+$ (100%); UPLC Purity: 95.93%, Ret.time: 5.60 min.

Example 2.55

3-(4-(5-Cyclohexyl-1,3,4-oxadiazol-2-yl)phenoxy)-5-((1-methoxypropan-2-yl)oxy)-N-(5-methylthiazol-2-yl)benzamide $^1$H NMR (400 MHz, CDCl$_3$) δ ppm: 1.32 (d, J=6.4 Hz, 3 H), 1.42-1.45 (m, 3 H), 1.70-1.74 (m, 3 H), 1.85-1.89 (m, 2 H), 2.12-2.16 (m, 2 H), 2.38 (s, 3 H), 2.95-2.99 (m, 1 H), 3.39 (s, 3 H), 3.39-3.51 (m, 1 H), 3.55-3.59 (m, 1 H), 4.56-4.60 (m, 1 H), 6.86 (t, J=2 Hz, 1 H), 6.92 (s, 1 H), 7.11 (d, J=8.8 Hz, 2 H), 7.18 (t, J=2 Hz, 1 H), 7.32 (t, J=2 Hz, 1 H), 8.02 (d, J=8.8 Hz, 2 H); ESI MS m/z (relative intensities): 549.2 (M+H)$^+$ (100%); UPLC Purity: 97.17% Ret.time: 5.63 min.

Example 2.56

Ethyl 4-(tert-butoxymethyl)-2-(3-((1-methoxypropan-2-yl)oxy)-5-(4-(5-methyl-1,3,4-oxa diazol-2-yl)phenoxy)benzamido)thiazole-5-carboxylate $^1$H NMR (400 MHz, CDCl$_3$) δ ppm: 1.2 (s, 9 H), 1.28-1.38 (m, 6 H), 2.62 (s, 3 H), 3.41 (s, 3 H), 3.50-3.53 (m, 1 H), 3.57-3.61 (m, 1 H), 4.34 (q, J=72 Hz, 2 H), 4.61-4.62 (m, 1 H), 4.85 (s, 2 H), 6.89 (t, J=2.4 Hz, 1 H), 7.12 (d, J=8.8 Hz, 2 H), 7.14-7.15 (m, 1 H), 7.31 (t, J=2.4 Hz, 1 H), 8.02-8.05 (d, J=8.8 Hz, 2 H); ESI MS m/z (relative intensities): 625.0 (M+H)$^+$ (100%), 647.0 (M+Na)$^+$ (10%); UPLC Purity: 94.74%, Ret.time: 5.402 min.

Example 2.57

Ethyl 4-(hydroxymethyl)-2-(3((1-methoxypropan-2-yl)oxy)-5-(4-(5-methyl-1,3,4-oxadiazol-2-yl)phenoxy)benzamido)thiazole-5-carboxylate $^1$H NMR (400 MHz, DMSO-d$_6$) δ ppm: 1.07-1.30 (m, 6 H), 2.56 (s, 3 H), 3.30 (s, 3 H), 3.48-3.56 (m, 2 H), 4.25 (q, J=7.2 Hz, 2 H), 4.76-4.77 (m, 3 H), 5.10-5.12 (m, 1 H), 6.99 (t, J=2.0 Hz, 1 H), 7.23 (d, J=8.8 Hz, 2 H), 7.37 (t, J=2.0 Hz, 1 H), 7.58 (s, 1 H), 7.99 (d, J=8.8 Hz, 2 H), 13.2 (s, 1 H); ESI MS m/z (relative intensities): 568.8 (M+H)$^+$ (100%); UPLC Purity: 96.28%, Ret.time: 4.4 min.

Example 2.58

5-Chloro-2-(3-((1-methoxypropan-2-yl)oxy)-5-(4-(5-methyl-1,3,4-oxadiazol-2-yl)phenoxy)benzamido)-N,N-dimethylthiazole-4-carboxamide $^1$H NMR (400 MHz, DMSO-d$_6$) δ ppm: 1.31 (d, J=6.4 Hz, 3 H), 2.56 (s, 3 H), 2.92 (s, 3 H), 2.98 (s, 3 H), 3.31 (s, 3 H); 3.47-3.50 (m, 1 H), 3.57-3.61 (m, 1 H), 4.75-4.77 (m, 1 H), 6.99 (t, J=2 Hz, 1 H), 7.22 (d, J=8.8 Hz, 2 H); 7.34 (t, J=1.6 Hz, 1 H), 7.55 (s, 1 H), 8.01 (d, J=8.8 Hz, 2 H), 13.05 (s, 1 H); ESI MS m/z (relative intensities): 571.8 (M+H)$^+$ (100%); 593.8, (M+Na)$^+$ (75%); UPLC Purity: 91.85%, Ret.time: 4.41 min.

Example 2.59

5-Chloro-2-(3-((1-methoxypropan-2-yl)oxy)-5-(4-(5-methyl-1,3,4-oxadiazol-2-yl)phenoxy)benzamido)thiazole-4-carboxamide $^1$H NMR (400 MHz, DMSO-d$_6$) δ ppm: 1.25 (d, J=6.4 Hz, 3 H), 2.56 (s, 3 H), 3.31 (s, 3 H), 3.46-3.53 (m, 2 H), 4.75-4.79 (m, 1 H), 7.00 (t, J=2 Hz, 1 H), 7.22 (d, J=8.8 Hz, 2 H), 7.23-7.25 (m, 1 H), 7.27 (s, 1 H), 7.35 (s, 1 H), 7.55 (m, 1 H), 7.71 (m, 1 H), 8.01 (d, J=8.8 Hz, 2 H), 13.05 (s, 1 H); ESI MS m/z (relative intensities): 543.7 (M+H)$^+$, (100%), 565.9 (M+Na)$^+$ (95%); UPLC Purity: 91.70%, Ret.time: 4.10 min.

Example 2.60

2-(3-((1-Methoxypropan-2-yl)oxy)-5-(4-(5-methyl-1,3,4-oxadiazol-2-yl)phenoxy)benzamido)-N,N-dimethylthiazole-4-carboxamide $^1$H NMR (400 MHz, CDCl$_3$) δ ppm: 1.35 (d, J=6.4 Hz, 3 H), 2.62 (s, 3 H), 3.09 (s, 3 H), 3.19 (s, 3 H), 3.50 (s, 3 H), 3.51-3.53 (m, 1 H), 3.57-3.66 (m, 1 H), 4.60-4.64 (m, 1 H), 6.88 (t, J=2 Hz, 1 H), 7.13 (d, J=8.8 Hz, 2 H), 7.17 (t, J=1.6 Hz, 1 H), 7.29 (t, J=1.6 Hz, 1 H), 7.46 (s, 1 H), 8.01 (d, J=8.8 Hz, 2 H), 9.62 (bs, 1 H); ESI MS m/z (relative intensities): 538.1 (M+H)$^+$ (100%), 559.85 (M+Na)$^+$ (10%); UPLC Purity: 97.48%, Ret.time: 3.93 min.

Example 2.61

2-(3-((1-Methoxypropan-2-yl)oxy)-5-(4-(5-methyl-1,3,4-oxadiazol-2-yl)phenoxy)benzamido)thiazole-4-carboxamide $^1$H NMR (400 MHz, CDCl$_3$) δ ppm: 1.33 (d, J=6.4 Hz, 3 H), 2.61 (s, 3 H), 3.41 (s, 3 H), 3.50-3.53 (m, 1 H), 3.57-3.61 (m, 1 H), 4.63-4.67 (m, 1 H), 5.92 (s, 1 H), 6.89 (s, 2 H), 7.11 (d, J=8.8 Hz, 2 H), 7.24-7.26 (m, 1 H), 7.40 (t, J=1.6 Hz, 1 H), 7.81 (s, 1H), 8.02 (d, J=8.8 Hz, 2 H), 9.97 (bs, 1 H); ESI MS m/z (relative intensities): 509.9 (M+H)$^+$ (100%); UPLC Purity: 96.45%, Ret.time: 3.68 min.

Example 2.62

5-Chloro-2-(3-((1-methoxypropan-2-yl)oxy)-5-(4-(5-methyl-1,3,4-oxadiazol-2-yl)phenoxy)benzamido)thiazole-4-carboxylic acid $^1$H NMR (400 MHz, DMSO-d$_6$) δ ppm: 1.33 (d, J=6.4 Hz, 3 H), 2.61 (s, 3 H), 3.36 (s, 3 H), 3.45-3.48 (m, 1 H), 3.53-3.57 (m, 1 H), 4.55-4.57 (m, 1 H), 6.79 (s, 1 H), 7.11 (d, J=8.8 Hz, 2 H), 7.54-7.60 (m, 2 H), 8.02 (d, J=8.8 Hz, 2 H), 12.69 (bs, 1 H), 14.62 (bs, 1 H); ESI MS m/z (relative intensities): 544.90 (M+H)⁺ (10%), 568.91 (M+Na)⁺ (60%); UPLC Purity: 81.08%, Ret.time: 4.29 min.

Example 2.63

N-(4-formylthiazol-2-yl)-34(1-methoxypropan-2-yl)oxy)-5-(4-(5-methyl-1,3,4-oxadiazol-2-yl)phenoxy)benzamide $^1$H NMR (400 MHz, CDCl$_3$) δ ppm: 1.34 (d, J=6.4 Hz, 3 H), 2.62 (s, 3 H), 3.41 (s, 3 H), 3.50-3.54 (m, 1 H), 3.57-3.61 (m, 1 H), 4.60-4.64 (m, 1 H), 6.90 (t, J=2 Hz, 1 H), 7.12 (d, J=8.8 Hz, 2 H), 7.15 (s, 1 H), 7.31 (s, 1 H), 7.88 (s, 1 H), 8.04 (d, J=8.8 Hz, 2 H), 9.84 (s, 1 H), 10.1 (s, 1 H); ESI MS m/z (relative intensities): 494.9 (M+H)⁺ (100%); UPLC Purity: 97.98%, Ret.time: 4.12 min.

Example 2.64

3-((1-Methoxypropan-2-yl)oxy)-5-(4-(5-(tetrahydro-2H-pyran-4-yl)-1,3,4-oxadiazol-2-yl)phenoxy)-N-(thiazol-2-yl)benzamide $^1$H NMR (400 MHz, CDCl$_3$) δ ppm: 1.33 (d, J=6.4 Hz, 3 H), 2.01-2.10 (m, 4 H), 3.22-3.27 (m, 1 H), 3.4 (s, 3 H), 3.48-3.51 (m, 1 H), 3.52-3.62 (m, 3 H), 4.05-4.10 (m, 2 H), 4.58-4.62 (m, 1 H), 6.88 (t, J=2 Hz, 1 H), 6.99 (d, J=3.6 Hz, 1 H), 7.12 (d, J=8.8 Hz, 2 H), 7.19 (t, J=1.6 Hz, 1 H), 7.32-7.35 (m, 2 H), 8.01 (d, J=8.8 Hz, 2 H); ESI MS m/z (relative intensities): 537.1 (M+H)⁺ (100%); UPLC Purity: 93.43%, Ret.time: 4.31 min.

Example 2.65

3-((1-Methoxypropan-2-yl)oxy)-N-(4-methylthiazol-2-yl)-5-(4-(5-(tetrahydro-2H-pyran-4-yl)-1,3,4-oxadiazol-2-yl)phenoxy)benzamide $^1$H NMR (400 MHz, CDCl$_3$) δ ppm: 1.32 (d, J=6.4 Hz, 3 H), 2.02-2.10 (m, 4 H), 2.29 (s, 3 H), 3.22-3.26 (m, 1 H), 3.40 (s, 3 H), 3.48-3.51 (m, 1 H), 3.52-3.62 (m, 3 H), 4.05-4.10 (m, 2 H), 4.57-4.61 (m, 1 H), 6.56 (s, 1 H), 6.87 (t, J=2 Hz, 1 H), 7.08-7.11 (m, 1 H), 7.13 (d, J=8.8 Hz, 2 H), 7.28 (t, J=2 Hz, 1 H), 8.01-8.04 (m, 2 H); ESI MS m/z (relative intensities): 550.8 (M+H)⁺ (100%); UPLC Purity: 96.66%, Ret.time: 4.52 min.

Example 2.66

3-((1-Methoxypropan-2-yl)oxy)-N-(5-methylthiazol-2-yl)-5-(4-(5-(tetrahydro-2H-pyran-4-yl)-1,3,4-oxadiazol-2-yl)phenoxy)benzamide $^1$H NMR (400 MHz, CDCl$_3$) δ ppm: 1.32 (d, J=6.4 Hz, 3 H), 2.01-2.10 (m, 4 H), 2.39 (s, 3 H), 3.22-3.27 (m, 1 H), 3.39 (s, 3 H), 3.48-3.51 (m, 1 H), 3.54-3.61 (m, 3 H), 4.05-4.10 (m, 2 H), 4.58-4.62 (m, 1 H), 6.86 (t, J=2 Hz, 1 H), 6.96 (s, 1 H), 7.12 (d, J=8.8 Hz, 2 H), 7.18 (t, J=2 Hz, 1 H), 7.33 (t, J=1.6 Hz, 1 H), 8.01-8.03 (d, J=8.8 Hz, 2 H); ESI MS m/z (relative intensities): 550.9 (M+H)⁺ (100%); UPLC Purity: 95.44%, Ret.time: 4.52 min.

Example 2.67

N-(5-(Hydroxymethyl)thiazol-2-yl)-3-((1-methoxypropan-2-yl)oxy)-5-(4-(5-methyl-1,3,4-oxadiazol-2-yl)phenoxy)benzamide $^1$H NMR (400 MHz, DMSO-d$_6$) δ ppm: 1.22 (d, J=6 Hz, 3 H), 2.56 (s, 3 H), 3.31 (s, 3 H), 3.45-3.53 (m, 2 H), 4.59 (d, J=6 Hz, 2 H), 4.75-4.79 (m, 1 H), 5.38 (t, J=5.6 Hz, 1 H), 6.95 (t, J=2.4 Hz, 1 H), 7.22 (d, J=8.8 Hz, 2 H), 7.34 (t, J=1.6 Hz, 2 H), 7.55 (t, J=2 Hz, 1 H), 8.01 (d, J=8.8 Hz, 2 H), 12.52 (bs, 1 H); ESI MS m/z (relative intensities): 496.9 (M+H)⁺ (100%); UPLC Purity: 96.3%, Ret.time: 3.63 min.

Example 2.68

N-(5-Formylthiazol-2-yl)-3-((1-methoxypropan-2-yl)oxy)-5-(4-(5-methyl-1,3,4-oxadiazol-2-yl)phenoxy)benzamide $^1$H NMR (400 MHz, DMSO-d$_6$) δ ppm: 1.24 (d, J=6 Hz, 3 H), 2.56 (s, 3 H), 3.30 (s, 3 H), 3.45-3.53 (m, 2 H), 4.46-4.80 (m, 1 H), 7.01 (t, J=2.4 Hz, 1 H), 7.23 (d, J=8.8 Hz, 2 H), 7.38 (d, J=1.6 Hz, 1 H), 7.58 (s, 1 H), 8.01 (d, J=8.8 Hz, 2 H), 8.48 (s, 1 H), 9.98 (s, 1 H), 13.24 (bs, 1 H); ESI MS m/z (relative intensities): 494.9 (M+H)⁺ (85%); UPLC Purity: 95.54%, Ret.time: 4.15 min.

Example 2.69

2-(3-((1-Methoxypropan-2-yl)oxy)-5-(4-(5-methyl-1,3,4-oxadiazol-2-yl)phenoxy)benzamido)-N,N-dimethylthiazole-5-carboxamide $^1$H NMR (400 MHz, DMSO-d$_6$) δ ppm: 1.23 (d, J=6 Hz, 3 H), 2.48 (s, 6 H), 2.53 (s, 3 H), 3.31 (s, 3 H), 3.45-3.53 (m, 2 H), 4.76-4.80 (m, 1 H), 6.98 (t, J=2 Hz, 1 H), 7.25 (d, J=8.8 Hz, 2 H), 7.36 (t, J=1.6 Hz, 1 H), 7.57 (t, J=1.6 Hz, 1 H), 7.94 (s, 1 H); 7.99 (d, J=8.8 Hz, 2 H), 12.8 (bs, 1 H); ESI MS m/z (relative intensities): 538.1 (M+H)⁺ (100%), 559.85 (M+Na)⁺ (10%); UPLC Purity: 96.11%, Ret.time: 3.85 mM.

Example 2.70

2-(3-((1-methoxypropan-2-yl)oxy)-5-(4-(5-methyl-1,3,4-oxadiazol-2-yl)phenoxy)benzamido)thiazole-5-carboxamide $^1$H NMR (400 MHz, DMSO-d$_6$) δ ppm: 1.24 (d, J=6 Hz, 3 H), 2.56 (s, 3 H), 3.30 (s, 3 H), 3.45-3.50 (m, 2 H), 4.75-4.85 (m, 1 H), 6.97 (t, J=2 Hz, 1 H), 7.22 (d, J=6.8 Hz, 2 H), 7.35 (t, J=1.6 Hz, 1 H), 7.45 (bs, 1 H), 7.55 (s, 1 H), 8.00 (d, J=6.8 Hz, 2 H), 8.11 (s, 1 H), 12.8 (bs, 1 H); ESI MS m/z (relative intensities): 509.9 (M+H)⁺, 100%; 531.6, 20% (M+Na)⁺; UPLC Purity: 97.24%, Ret.time: 3.569 min.

Testing of Compounds of the Invention Using In-Vitro Assay

The compound of the invention was incubated with glucokinase (GK) enzyme (0.2 units) for 10 minutes in assay buffer at 26° C. After incubation, addition of glucose-6-phosphate dehydrogenase (2.5 units), ATP (1 mM) and glucose (2.5 mM). Absorbance is measured at 340 nM for 15 minutes with 10 second interval using UV transparent plate in kinetic mode on Spectramax-190 at 30° C.

The results obtained from the above test using representative compounds of the formula (I) as the test compound are summarized in the following tables (Table 1 and Table 2):

TABLE 1

| Example No. | % of GK activity wrt DMSO | | | |
|---|---|---|---|---|
| | 0.1 uM | 1 uM | 5 uM | 10 uM |
| 1.1 | 275.8 | 308.7 | 315.9 | 308.7 |
| 1.2 | 167 | 229.1 | 242.4 | 244 |
| 1.3 | 99.85 | 96.8 | 109.9 | 106.9 |
| 1.4 | 282 | 313.1 | 314.3 | 311.2 |
| 1.5 | 233.9 | 292.1 | 305.1 | 293.1 |
| 1.6 | 134.1 | 177.5 | 182.7 | 165.3 |
| 1.7 | 164.2 | 228 | 244.8 | 235.6 |
| 1.9 | 121.83 | 137.7 | 141.3 | 153.4 |
| 2.1 | 271.4 | 267 | 271 | 282.3 |
| 2.2 | 145.9 | 178.5 | 192.9 | 192.1 |
| 2.3 | 122.9 | 136.9 | 148.5 | 150.4 |
| 2.4 | 240.5 | 283.5 | 324.4 | 310.8 |
| 2.5 | 195.4 | 256.2 | 282 | 278.2 |
| 2.6 | 128.2 | 196.4 | 251.8 | 249.3 |
| 2.7 | 288.5 | 348.9 | 353 | 345.4 |
| 2.8 | 239.5 | 323.6 | 336.3 | 328.9 |
| 2.9 | 250.8 | 277.9 | 283.2 | 278.9 |
| 2.01 | 310 | 370 | 368.5 | 356.4 |
| 2.11 | 235.2 | 257.5 | 191 | 243.2 |
| 2.12 | 139.5 | 175.5 | 302.2 | 143.6 |
| 2.13 | 111.5 | 180.5 | 232.7 | 214.6 |
| 2.14 | 115.7 | 184.4 | 241 | 214.6 |
| 2.15 | 104.8 | 163.6 | 239 | 265.5 |
| 2.16 | 101.27 | 143.9 | 200.9 | 205.05 |
| 2.17 | 113 | 170.18 | 306.22 | 349.86 |
| 2.18 | 104.9 | 149.16 | 251.07 | 260.38 |
| 2.19 | 105.77 | 188.48 | 317.63 | 343.54 |
| 2.02 | 250.82 | 405.21 | 435.77 | 408.30 |
| 2.21 | 178.8 | 287.3 | 317.5 | 292.8 |
| 2.22 | 152.9 | 323.3 | 435.6 | 418.3 |
| 2.25 | 223.9 | 383.9 | 439.2 | 417.8 |
| 2.28 | 223.3 | 449.6 | 493.4 | 488.5 |
| 2.31 | 252.3 | 433.6 | 518.5 | 470.8 |
| 2.36 | 209.7 | 270.6 | 316.33 | 301.7 |
| 2.42 | 125.6 | 223.4 | 306.1 | 333.2 |

TABLE 2

| Ex. No. | EC$_{50}$ (nM) |
|---|---|
| 1.1 | 21 |
| 1.2 | 81 |
| 1.4 | 23 |
| 1.5 | 88 |
| 2.1 | 14 |
| 2.2 | 316 |
| 2.4 | 64 |
| 2.5 | 103 |

The novel compounds of the present invention can be formulated into suitable pharmaceutically acceptable compositions by combining with suitable excipients by techniques and processes and concentrations as are well known. Thus, a pharmaceutical composition comprising the compounds of the present invention may comprise a suitable binder, suitable bulking agent &/or diluent and any other suitable agents as may be necessary. Optionally, the pharmaceutical composition may be suitably coated with suitable coating agents.

The compounds of Formula (I) or pharmaceutical compositions containing them are useful as antidiabetic compounds suitable for humans and other warm blooded animals, and may be administered either by oral, topical or parenteral administration. The compounds of the present invention of Formula (I) are glucokinase activators and are useful in the treatment of disease states mediated by glucokinase.

The quantity of active component, that is, the compounds of Formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

While the present invention has been described in terms of its specific embodiments, certain modifications and equivalents will be apparent to those skilled in the art and are intended to be included within the scope of the present invention.

I claim:

1. Compounds having the structure of Formula (I),

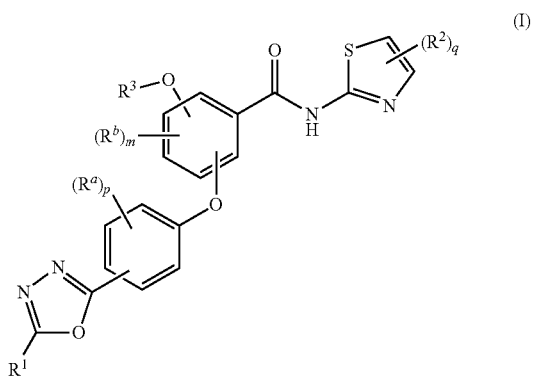

and their pharmaceutically acceptable salts, pharmaceutically acceptable enantiomers, diastereomers, wherein $R^1$ and $R^3$ are independently selected from halo, cyano, or optionally substituted groups selected from amino, $C_{1-6}$ alkyl, $C_{2-6}$ alkenyl, $C_{2-6}$ alkynyl, aryl, cycloalkyl, carbocycle, heterocycloalkyl, cycloalkyl($C_{1-6}$)alkyl, or heterocycloalkyl($C_{1-6}$)alkyl groups; n=0, 1, 2; m =0,1,2, 3; & p=0,1,2,3,4; $R^2$ at each occurrence is independently selected from halo, amino, cyano, nitro, ($C_{1-4}$)alkyl, ($C_{2-6}$) alkenyl, ($C_{2-6}$)alkynyl, —(CH$_2$)$_n$COO(C$_{1-4}$) alkyl, —(CH$_2$)$_n$COOH, S(O)$_n$, S(O)$_n$NH$_2$, or S(O)$_n$NH (C$_{1-6}$)alkyl; q=0, 1, 2; and $R^a$ & $R^b$ at each occurrence is independently selected from halo, cyano, nitro, hydroxyl, or optionally substituted groups selected from alkoxy, perfluoroalkoxy, amino, C$_{1-4}$alkyl, C$_{2-6}$ alkenyl, C$_{2-6}$ alkynyl, cycloalkyl, —(CH$_2$)$_n$COO(C$_{1-4}$)alkyl, or —(CH$_2$)$_n$COOH groups, wherein the groups representing $R^1$, $R^2$, $R^3$, and $R^a$ and $R^b$ may be further substituted on available carbon atom with one or three substituent (s).

2. The compounds of Formula (I) as claimed in claim 1, wherein $R^3$ is selected from the following groups:

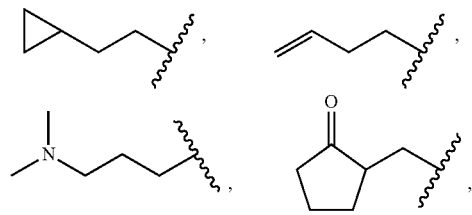

-continued

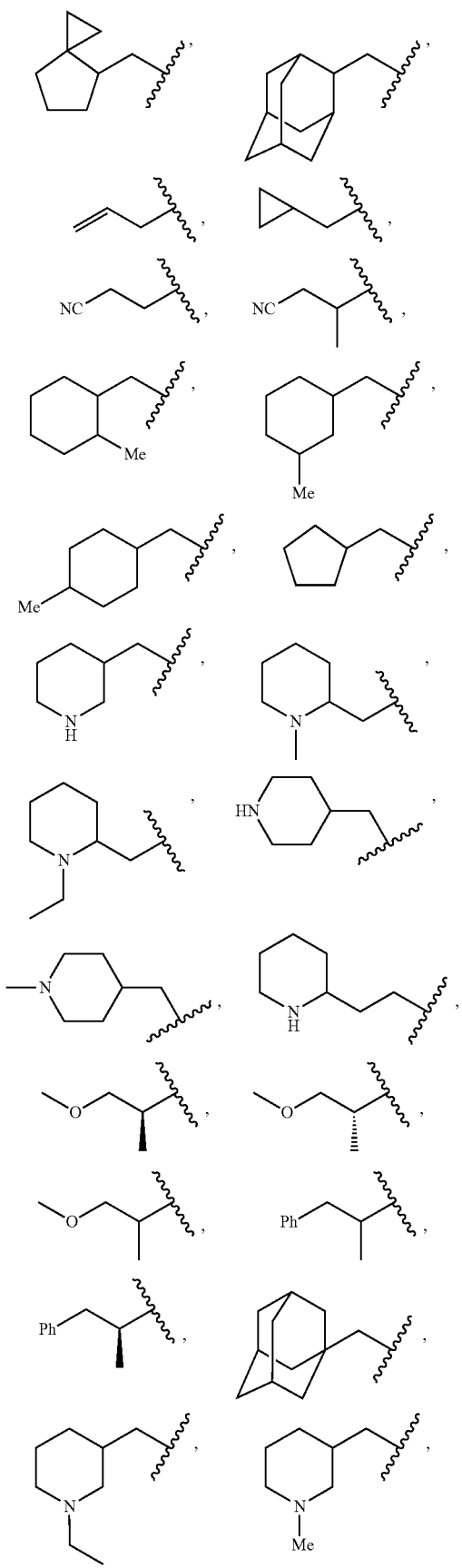

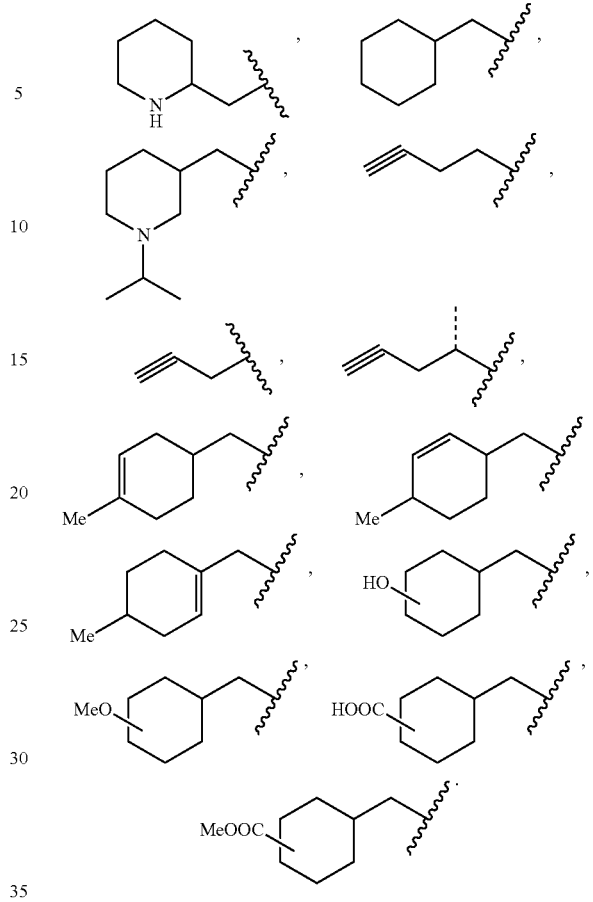

3. The compounds as claimed in claim 1 wherein the substitutions on $R^1$ is selected from one to three substituent(s) independently selected from hydroxy, $(C_{1-4})$alkoxy, halo, cyano, amino, $(C_{1-6})$alkylamino, nitro, $COO(C_{1-4})$ alkyl, $S(O)_n$, $S(O)_nNH_2$, $S(O)_nNH(C_{1-6})$alkyl, $C(O)$; or $C(O)NH(C_{1-6})$alkyl groups.

4. The compounds as claimed in claim 1, wherein the substitutions on $R^2$ is selected from one to three substituent(s) independently selected from hydroxy, halo, cyano, nitro, optionally substituted groups selected from $(C_{1-4})$alkoxy, amino, $(C_{1-6})$alkylamino, di$(C_{1-6})$alkylamino, $COO(C_{1-4})$ alkyl, $S(O)_n$, $S(O)_nNH_2$, or $S(O)_nNH(C_{1-6})$alkyl groups.

5. The compounds as claimed in claim 1 wherein the substitutions on $R^a$ and $R^b$ are independently selected from one to three substituent(s) independently selected from hydroxy, $(C_{1-4})$alkoxy, halo, cyano, amino, $(C_{1-6})$ alkylamino, nitro, $COO(C_{1-4})$alkyl, $S(O)_n$, $S(O)_nNH_2$, $S(O)_nNH(C_{1-6})$alkyl, $C(O)$; or $C(O)NH(C_{1-6})$alkyl groups.

6. A compound selected from the group consisting of:
   3-(But-3-enyloxy)-5-(4-(5-methyl-1,3,4-oxadiazol-2-yl)phenoxy)-N-(thiazol-2-yl)benzamide;
   3-(But-3-enyloxy)-5-(4-(5-ethyl-1,3,4-oxadiazol-2-yl)phenoxy)-N-(thiazol-2-yl)benzamide;
   3-(But-3-enyloxy)-5-(4-(5-isopropyl-1,3,4-oxadiazol-2-yl)phenoxy)-N-(thiazol-2-yl)benzamide;
   3-(But-3-enyloxy)-5-(4-(5-cyclopropyl-1,3,4-oxadiazol-2-yl)phenoxy)-N-(thiazol-2-yl)benzamide;
   3-(4-(5-cyclopropyl-1,3,4-oxadiazol-2-yl)phenoxy)-5-(2-cyclopropylethoxy)-N-(thiazol-2-yl)benzamide;
   3-(2-cyclopropylethoxy)-5-(4-(5-ethyl-1,3,4-oxadiazol-2-yl)phenoxy)-N-(thiazol-2-yl)benzamide;

3-(2-Cyclopropylethoxy)-5-(4-(5-isopropyl-1,3,4-oxadiazol-2-yephenoxy)-N-(thiazol-2-yl)benzamide;
3-(2-Cyclopropylethoxy)-5-(4-(5-isobutyl-1,3,4-oxadiazol-2-yl)phenoxy)-N-(thiazol-2-yl)benzamide;
3-(But-3-enyloxy)-5-(4-(5-isobutyl-1,3,4-oxadiazol-2-yl)phenoxy)-N-(thiazol-2-yl)benzamide 3-(Cyclohexylmethoxy)-5-(4-(5-isobutyl-1,3,4-oxadiazol-2-yl)phenoxy)-N-(thiazol-2-yl)benzamide;
3-(4-(5-isobutyl-1,3,4-oxadiazol-2-yl)phenoxy)-5-(piperidin-3-ylmethoxy)-N-(thiazol-2-yl)benzamide;
3-(1-Cyanopropan-2-yloxy)-5-(4-(5-cyclopropyl-1,3,4-oxadiazol-2-yl)phenoxy)-N-(thiazol-2-yl)benzamide;
3-(1-Cyanopropan-2-yloxy)-5-(4-(5-isopropyl-1,3,4-oxadiazol-2-yl)phenoxy)-N-(thiazol-2-yl)benzamide;
3-(1-Cyanopropan-2-yloxy)-5-(4-(5-ethyl-1,3,4-oxadiazol-2-yl)ephenoxy)-N-(thiazol-2-yl)benzamide;
3-(4-(5-methyl-1,3,4-oxadiazol-2-yl)phenoxy)-5-((4-methylcyclohexyl)methoxy)-N-(thiazol-2-yl)benzamide;
3-(4-(5-Methyl-1,3,4-oxadiazol-2-yl)phenoxy)-5((3-methylcyclohexyl)methoxy)-N-(thiazol-2-yl)benzamide;
3-(4-(5-methyl-1,3,4-oxadiazol-2-yl)phenoxy)-5-(piperidin-4-ylmethoxy)-N-(thiazol-2-yl)benzamide;
3-(4-(5-Methyl-1,3,4-oxadiazol-2-yl)phenoxy)-5-((1-methylpiperidin-4-yl)methoxy)-N-(thiazol-2-yl)benzamide;
3-(4-(5-methyl-1,3,4-oxadiazol-2-yl)phenoxy)-5-methylpiperidin-3-yl)methoxy)-N-(thiazol-2-yl)benzamide;
3-(4-(5-Methyl-1,3,4-oxadiazol-2-yl)phenoxy)-5-(piperidin-3-ylmethoxy)-N-(thiazol-2-yl)benzamide;
3-(2-Cyanoethoxy)-5-(4-(5-methyl-1,3,4-oxadiazol-2-yl)phenoxy)-N-(thiazol-2-yl)benzamide;
3-(Cyclopropylmethoxy)-5-(4-(5-methyl-1,3,4-oxadiazol-2-yl)phenoxy)-N-(thiazol-2-yl)benzamide;
3-(Allyloxy)-5-(4(5-methyl-1,3,4-oxadiazol-2-yl)phenoxy)-N-(thiazol-2-yl)Benzamide;
3-(1-Cyanopropan-2-yloxy)-5-(4-(5-methyl-1,3,4-oxadiazol-2-yl)phenoxy)-N-(thiazol-2-yl)benzamide;
3-(4-(5-Methyl-1,3,4-oxadiazol-2-yl)phenoxy)-5-(spiro[2.4]heptan-5-ylmethoxy)-N-(thiazol-2-yl)benzamide;
3-(4-(5-Methyl-1,3,4-oxadiazol-2-yl)phenoxy)-5-((3-oxocyclopentyl)methoxy)-N-(thiazol-2-yl)benzamide;
3-(1-Methoxypropan-2-yloxy)-5-(4-(5-methyl-1,3,4-oxadiazol-2-yl)phenoxy)-N-(thiazol-2-yl)benzamide;
3-(1-Methoxybutan-2-yloxy)-5-(4-(5-methyl-1,3,4-oxadiazol-2-yl)phenoxy)-N-(thiazol-2-yl)benzamide;
3-(1-Methoxy-3-methylbutan-2-yloxy)-5-(4-(5-methyl-1,3,4-oxadiazol-2-yl)phenoxy)-N-(thiazol-2-yl)benzamide;
3-(4-(5-Ethyl-1,3,4-oxadiazol-2-yl)phenoxy)-5-(1-methoxypropan-2-yloxy)-N-(thiazol-2-yl)benzamide;
3-(4-(5-iso-Propyl-1,3,4-oxadiazol-2-yl)phenoxy)-5-(1-methoxypropan-2-yloxy)-N-(thiazol-2-yl)benzamide;
3-(4-(5-Cyclopropyl-1,3,4-oxadiazol-2-yl)phenoxy)-5-(1-methoxypropan-2-yloxy)-N-(thiazol-2-yl)benzamide;
3-(4-(5-Cyclobutyl-1,3,4-oxadiazol-2-yl)phenoxy)-5-(1-methoxypropan-2-yloxy)-N-(thiazol-2-yl)benzamide;
3-(But-3-enyloxy)-5-(4-(5-methyl-1,3,4-oxadiazol-2-yl)phenoxy)-N-(thiazol-2-yl)benzamide 3-(2-Cyclopropylethoxy)-5-(4-(5-methyl-1,3,4-oxadiazol-2-yl)phenoxy)-N-(thiazol-2-yl)benzamide;
3-(3-(Dimethylamino)propoxy)-5-(4-(5-methyl-1,3,4-oxadiazol-2-yl)phenoxy)-N-(thiazol-2-yl)benzamide;
3-(Cyclohexylmethoxy)-5-(4-(5-methyl-1,3,4-oxadiazol-2-yl)phenoxy)-N-(thiazol-2-yl)benzamide;
3-(Cyclopentylmethoxy)-5-(4-(5-methyl-1,3,4-oxadiazol-2-yl)phenoxy)-N-(thiazol-2-yl)Benzamide;
3-(4-(5-iso-Propyl-1,3,4-oxadiazol-2-yl)phenoxy)-5-(piperidin-3-ylmethoxy)-N-(thiazol-2-yl)benzamide;
5-(1-Methoxypropan-2-yloxy)-2-(4-(5-methyl-1,3,4-oxadiazol-2-yl)phenoxy)-N-(thiazol-2-yl)benzamide;
2-(4-(5-Ethyl-1,3,4-oxadiazol-2-yl)phenoxy)-5-(1-methoxypropan-2-yloxy)-N-(thiazol-2-yl)benzamide;
2-(4-(5-iso-Propyl-1,3,4-oxadiazol-2-yl)phenoxy)-5-(1-methoxypropan-2-yloxy)-N-(thiazol-2-yl)benzamide;
2-(4-(5-Cyclopropyl-1,3,4-oxadiazol-2-yl)phenoxy)-5-(1-methoxypropan-2-yloxy)-N-(thiazol-2-yl)benzamide;
2-(4-(5-iso-butyl-1,3,4-oxadiazol-2-yl)phenoxy)-5-(1-methoxypropan-2-yloxy)-N-(thiazol-2-yl)benzamide;
(S)-5-(1-Methoxypropan-2-yloxy)-2-(4-(5-methyl-1,3,4-oxadiazol-2-yl)phenoxy)-N-(thiazol-2-yl)benzamide;
(S)-3-(1-Methoxypropan-2-yloxy)-5-(4-(5-methyl-1,3,4-oxadiazol-2-yl)phenoxy)-N-(thiazol-2-yl)benzamide;
(S)-3-(1-Methoxypropan-2-yloxy)-5-(4-(5-methyl-1,3,4-oxadiazol-2-yl)phenoxy)-N-(thiazol-2-yl)benzamide;
(S)-3-(4-(5-Ethyl-1,3,4-oxadiazol-2-yl)phenoxy)-5-(1-methoxypropan-2-yloxy)-N-(thiazol-2-yl)benzamide;
(S)-3-(4-(5-iso-Propyl-1,3,4-oxadiazol-2-yl)phenoxy)-5-(1-methoxypropan-2-yloxy)-N-(thiazol-2-yl)benzamide;
(S)-2-(4-(5-iso-Propyl-1,3,4-oxadiazol-2-yl)phenoxy)-4-(1-methoxypropan-2-yloxy)-N-(thiazol-2-yl)benzamide;
(S)-2-(4-(5-Ethyl-1,3,4-oxadiazol-2-yephenoxy)-4-(1-methoxypropan-2-yloxy)-N-(thiazol-2-yl)benzamide;
4-(1-Methoxypropan-2-yloxy)-2-(4-(5-methyl-1,3,4-oxadiazol-2-yl)phenoxy)-N-(4-methylthiazol-2-yl)benzamide;
N-(4-Chlorothiazol-2-yl)-4-(1-methoxypropan-2-yloxy)-2-(4-(5-methyl-1,3,4-oxadiazol-2-yl)phenoxy)benzamide;
N-(4-Fluorothiazol-2-yl)-4-(1-methoxypropan-2-yloxy)-2-(4-(5-methyl-1,3,4-oxadiazol-2-yl)phenoxy)benzamide;
4-(1-Methoxypropan-2-yloxy)-2-(4-(5-methyl-1,3,4-oxadiazol-2-yl)phenoxy)-N-(5methylthiazol-2-yl)benzamide;
N-(5-Chlorothiazol-2-yl)-4-(1-methoxypropan-2-yloxy)-2-(4-(5-methyl-1,3,4-oxadiazol-2-yl)phenoxy)benzamide;
N-(5-Fluorothiazol-2-yl)-4-(1-methoxypropan-2-yloxy)-2-(4-(5-methyl-1,3,4-oxadiazol-2-yl)phenoxy)benzamide;
(S)-N-(5-Fluorothiazol-2-yl)-4-(1-methoxypropan-2-yloxy)-2-(4-(5-methyl-1,3,4-oxadiazol-2-yl)phenoxy)benzamide;
(S)-N-(5-Fluorothiazol-2-yl)-3-(1-methoxypropan-2-yloxy)-5-(4-(5-methyl-1,3,4-oxadiazol-2-yl)phenoxy)benzamide;
4-(Allyloxy)-N-(5-fluorothiazol-2-yl)-2-(4-(5-methyl-1,3,4-oxadiazol-2-yl)phenoxy) benzamide;
4-(But-3-enyloxy)-N-(5-fluorothiazol-2-yl)-2-(4-(5-methyl-1,3,4-oxadiazol-2-yl)phenoxy) benzamide;
4-(But-3-enyloxy)-2-(4-(5-ethyl-1,3,4-oxadiazol-2-yl)phenoxy)-N-(5-fluorothiazol-2-yl)benzamide;
4-(But-3-enyloxy)-N-(5-fluorothiazol-2-yl)-2-(4-(5-isopropyl-1,3,4-oxadiazol-2-yl) phenoxy) benzamide;
4-(But-3-enyloxy)-2-(4-(5-cyclopropyl-1,3,4-oxadiazol-2-yl)phenoxy)-N-(5-fluorothiazol-2-yl)benzamide;

4-(But-3-enyloxy)-N-(5-fluorothiazol-2-yl)-2-(4-(5-phenyl-1,3,4-oxadiazol-2-yl)phenoxy) benzamide;

4-(But-3-enyloxy)-2-(4-(5-cyano-1,3,4-oxadiazol-2-yl)phenoxy)-N-(5-fluorothiazol-2-yl) benzamide;

4-(But-3-enyloxy)-N-(5-fluorothiazol-2-yl)-2-(4-(5-(2-methoxyethyl)-1,3,4-oxadiazol-2-yl) phenoxy)benzamide;

4-(But-3-enyloxy)-N-(5-fluorothiazol-2-yl)-2-(4-(5-(2-hydroxyethyl)-1,3,4-oxadiazol-2-yl) phenoxy)benzamide;

3-(But-3-enyloxy)-N-(5-fluorothiazol-2-yl)-5-(4-(5-(2-hydroxyethyl)-1,3,4-oxadiazol-2-yl) phenoxy)benzamide;

3-(But-3-enyloxy)-N-(5-fluorothiazol-2-yl)-5-(4-(5-(2-methoxyethyl)-1,3,4-oxadiazol-2-yl) phenoxy)benzamide;

3-(2-Cyclopropylethoxy)-N-(5-fluorothiazol-2-yl)-5-(4-(5-(2-methoxyethyl)-1,3,4-oxadiazol-2-yl)phenoxy) benzamide;

3-(2-Cyclopropylethoxy)-N-(5-fluorothiazol-2-yl)-5-(4-(5-(2-hydroxyethyl)-1,3,4-oxadiazol-2-yl)phenoxy) benzamide;

4-((1-Ethylpiperidin-4-yl)methoxy)-2-(4-(5-methyl-1,3,4-oxadiazol-2-yl)phenoxy)-N-(5-methylthiazol-2-yl)benzamide;

4-((1-Ethylpiperidin-4-yl)methoxy)-N-(5-fluorothiazol-2-yl)-2-(4-(5-methyl-1,3,4-oxadiazol-2-yl)phenoxy) benzamide;

4-(1-Cyanopropan-2-yloxy)-N-(5-fluorothiazol-2-yl)-2-(4-(5-methyl-1,3,4-oxadiazol-2-yl) phenoxy)benzamide;

N-(5-Chlorothiazol-2-yl)-4-(1-cyanopropan-2-yloxy)-2-(4-(5-methyl-1,3,4-oxadiazol-2-yl) phenoxy)benzamide;

4-(1-Cyanopropan-2-yloxy)-2-(4-(5-methyl-1,3,4-oxadiazol-2-yl)phenoxy)-N-(4-methyl thiazol-2-yl)benzamide;

3-(But-3-enyloxy)-5-(3-(5-cyclopropyl-1,3,4-oxadiazol-2-yl)phenoxy)-N-(thiazol-2-yl) benzamide;

3-(3-(5-Cyclopropyl-1,3,4-oxadiazol-2-yl)phenoxy)-5-(1-methoxypropan-2-yloxy)-N-(thiazol-2-yl)benzamide;

(R)-3-(3-(5-Cyclopropyl-1,3,4-oxadiazol-2-yl)phenoxy)-5-(1-methoxypropan-2-yloxy)-N-(thiazol-2-yl) benzamide;

(R)-3-(1-methoxypropan-2-yloxy)-5-(3-(5-methyl-1,3,4-oxadiazol-2-yl)phenoxy)-N-(thiazol-2-yl)benzamide;

(R)-3-(3-(5-ethyl-1,3,4-oxadiazol-2-yl)phenoxy)-5-(1-methoxypropan-2-yloxy)-N-(thiazol-2-yl)benzamide;

(R)-3-(3-(5-isopropyl-1,3,4-oxadiazol-2-yl)phenoxy)-5-(1-methoxypropan-2-yloxy)-N-(thiazol-2-yl)benzamide;

(R)-3-(3-(5-cyano-1,3,4-oxadiazol-2-yl)phenoxy)-5-(1-methoxypropan-2-yloxy)-N-(thiazol-2-yl)benzamide;

(R)-3-(3-(5-cyano-1,3,4-oxadiazol-2-yl)phenoxy)-5-(1-methoxypropan-2-yloxy)-N-(5-methylthiazol-2-yl) benzamide;

(R)-3-(3-(5-Cyano-1,3,4-oxadiazol-2-yl)phenoxy)-N-(5-fluorothiazol-2-yl)-5-(1-methoxypropan-2-yloxy)benzamide;

(R)-N-(5-Chlorothiazol-2-yl)-3-(3-(5-cyano-1,3,4-oxadiazol-2-yl)phenoxy)-5-(1-methoxypropan-2-yloxy) benzamide;

(R)-N-(5-Chlorothiazol-2-yl)-3-(1-methoxypropan-2-yloxy)-5-(3-(5-methyl-1,3,4-oxadiazol-2-yl)phenoxy) benzamide;

(R)-N-(5-Fluorothiazol-2-yl)-3-(1-methoxypropan-2-yloxy)-5-(3-(5-methyl-1,3,4-oxadiazol-2-yl)phenoxy) benzamide; and (R)-3-(3-(5-Ethyl-1,3,4-oxadiazol-2-yl)phenoxy)-N-(5-fluorothiazol-2-yl)-5-(1-methoxy propan-2-yloxy)benzamide, or their pharmaceutically acceptable salts, pharmaceutically acceptable enantiomers, diastereomers.

7. A pharmaceutical composition comprising a therapeutically effective amount of a compound of Formula (I) as claimed in claim 1 and one or more pharmaceutically acceptable carriers, diluents or excipients.

8. The pharmaceutical composition according to claim 7 which is useful for increasing insulin secretion for treating type II diabetes.

9. A method of treating type II diabetes comprising administering to a patient in need thereof an effective amount of a compound of Formula (I) according to claim 1 or 6 or its pharmaceutical composition according to claim 7 or 8.

10. A pharmaceutical composition comprising a therapeutically effective amount of a compound of Formula (I) as claimed in claim 6 and one or more pharmaceutically acceptable carriers, diluents or excipients.

* * * * *